(12) United States Patent
Umezawa et al.

(10) Patent No.: US 7,755,305 B2
(45) Date of Patent: Jul. 13, 2010

(54) CHARGED PARTICLE BEAM EXTRACTION SYSTEM AND METHOD

(75) Inventors: Masumi Umezawa, Mito (JP); Kazuo Hiramoto, Hitachiohta (JP); Koji Matsuda, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 222 days.

(21) Appl. No.: 12/129,145

(22) Filed: May 29, 2008

(65) Prior Publication Data
US 2009/0283702 A1 Nov. 19, 2009

(30) Foreign Application Priority Data
May 14, 2008 (JP) .............................. 2008-127150

(51) Int. Cl.
H05H 13/04 (2006.01)
H05H 7/10 (2006.01)
A61N 5/10 (2006.01)

(52) U.S. Cl. .................... 315/507; 315/503; 313/363.1; 250/396 R; 250/492.3

(58) Field of Classification Search ................. 315/507, 315/503; 313/363.1; 250/396 R, 492.3
See application file for complete search history.

(56) References Cited

U.S. PATENT DOCUMENTS 5,363,008 A 11/1994 Hiramoto et al.
7,385,203 B2* 6/2008 Nakayama et al. .......... 250/400
2008/0067405 A1* 3/2008 Nihongi et al. ............. 250/398
2008/0067452 A1* 3/2008 Moriyama et al. ....... 250/503.1
2010/0001212 A1* 1/2010 Nishiuchi et al. ........ 250/492.3

FOREIGN PATENT DOCUMENTS
JP 09-223600 8/1997

OTHER PUBLICATIONS

Chu, W. T., et al, "Instrumentation for treatment of cancer using proton and light-ion beams", Review of Scientific Instruments, vol. 64, No. 8, Aug. 1993, pp. 2077-2078 and Figs. 30 and 31.

* cited by examiner

Primary Examiner—Nikita Wells
(74) Attorney, Agent, or Firm—Mattingly & Malur, P.C.

(57) ABSTRACT

A charged particle beam extraction system and method capable of shortening the irradiation time and increasing the number of patients treatable per unit time. The charged particle beam extraction system comprises a synchrotron for cyclically performing patterned operation including four steps of introducing, accelerating, extracting and decelerating an ion beam, an on/off switch for opening or closing connection between an RF knockout electrode and an RF power supply for applying RF power to the RF knockout electrode, and a timing controller for controlling on/off-timing of the on/off switch such that when extraction of the ion beam is stopped at least once during the extraction step of the synchrotron, an amount of the ion beam extracted from the synchrotron in one cycle is held substantially at a setting value.

12 Claims, 14 Drawing Sheets

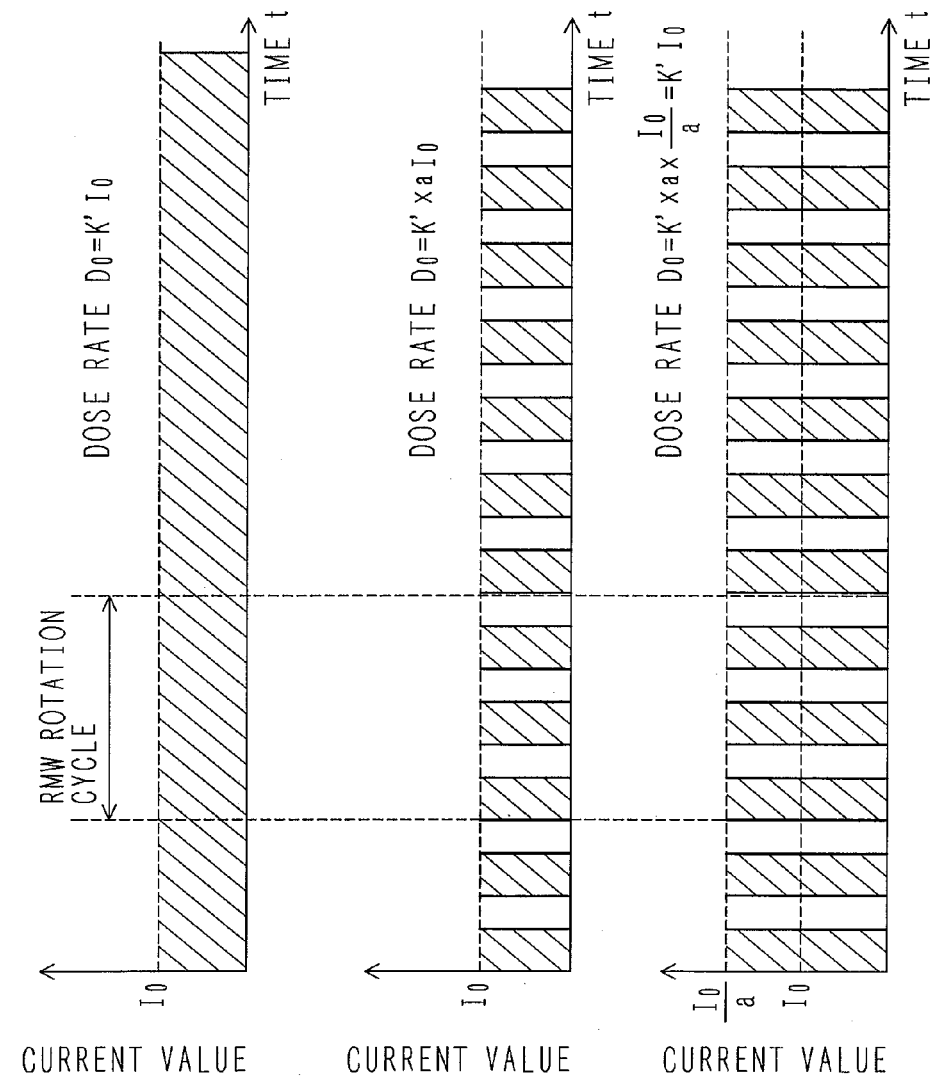

CHARGED PARTICLE BEAM EXTRACTION SYSTEM AND METHOD

BACKGROUND OF THE INVENTION

1. Field of the Invention

The present invention relates to a charged particle beam extraction system and method for extracting an ion beam, e.g., a proton or carbon ion beam, through an irradiation device.

2. Description of the Related Art

There is known a therapy method for irradiating an ion beam, e.g., a proton or carbon ion beam, to an affected part in the body of a patient, such as a cancer. A particle beam therapy system for use in such therapy comprises an ion beam generator, a beam line, and an irradiation device of the rotation type, for example. An ion beam accelerated by the ion beam generator reaches the irradiation device through a first beam line, and is irradiated to the affected part in the patient body from an irradiation nozzle having passed through a second beam line installed in the irradiation device. Known examples of the ion beam generator include means for circulating the ion beam along an orbit, means for bringing betatron oscillation of the ion beam into a resonant state outside the separatrix of resonance, and a circular accelerator provided with an extraction deflector for extracting the ion beam from the orbit (see, e.g., Patent Reference 1; U.S. Pat. No. 5,363,008).

The therapy using an ion beam, e.g., the treatment with irradiation of a proton beam, is based on characteristics that most of energy of the proton beam is released at the time when protons are stopped (to provide a Bragg peak). Then, the energy of the proton beam is selected to stop protons near the affected part in the patient body so that most of the energy (absorbed dose) is given only to cells of the affected part.

Usually, the affected part is present in some organ and therefore has a certain thickness in the direction of depth from the body surface of a patient (i.e., the direction of travel of the ion beam). To effectively irradiate the ion beam over the entire region of the affected part in the direction of thickness, the ion beam must be controlled so as to form a comparatively wide and flat range of absorbed dose in the direction of thickness (i.e., a spread-out Bragg peak, hereinafter referred to as an "SOBP").

From that point of view, a ridge filter has hitherto been proposed which includes a plurality of structures each shaped to have a thickness increasing or decreasing step by step and arranged cyclically in a direction perpendicular to the direction of travel of the ion beam, thereby changing the thickness of the filter, through which the ion beam passes, depending on the beam incident position (see, e.g., Non-Patent Document 1; "REVIEW OF SCIENTIFIC INSTRUMENTS", Vol. 64, No. 8 (August 1993), p. 2078 and FIG. 31). The ion beam is irradiated to the affected part in the patient body through the ridge filter. More specifically, when the ion beam passes an opening between the adjacent structures, the ion beam passes through the ridge filter without attenuating its energy and the Bragg peak is produced in a deep position inside the body. When the ion beam passes a thin step portion of the structure, the beam energy is slightly attenuated and the Bragg peak is produced in a middle position inside the body. When the ion beam passes a thick step portion of the structure, the beam energy is largely attenuated and the Bragg peak is produced in a shallow position near the body surface. Since the Bragg peaks are thus produced at different depths in the patient body, the SOBP can be obtained over a comparatively wide region from the position near the body surface to the position deep inside the body.

As another means for producing the SOBP, a range modulation wheel (hereinafter abbreviated to "RMW") has already been proposed which includes a plurality of blades each having a thickness increasing or decreasing step by step in the circumferential direction (see, e.g., Non-Patent Document 2; "REVIEW OF SCIENTIFIC INSTRUMENTS", Vol. 64, No. 8 (August 1993), p. 2077 and FIG. 30). The RMW is set in the travel path of the ion beam and is rotated in a plane perpendicular to the direction of travel of the ion beam. At the time when the ion beam enters an opening between the adjacent blades, the ion beam passes through the RMW without attenuating its energy and the Bragg peak is produced in a deep position inside the body. At the time when the ion beam passes a thin step portion of the blade, the beam energy is slightly attenuated and the Bragg peak is produced in a middle position inside the body. At the time when the ion beam passes a thick step portion of the blade, the beam energy is largely attenuated and the Bragg peak is produced in a shallow position near the body surface. With the rotation of the RMW, the position of the Bragg peak varies cyclically. As a result, the SOBP can be obtained over a comparatively wide region from the position near the body surface to the position deep inside the body, looking at the beam energy integrated over time.

On the other hand, as one irradiation method for improving a degree of matching of dose distribution with the shape of the affected part and minimizing useless dose irradiated to the surrounding organs, there is known a pencil-beam scanning method of scanning a pencil-shaped small-diameter beam in match with the shape of the affected part. Regarding an irradiation technique for use with the pencil beam scanning method, it is proposed to divide an irradiation area into small targets (referred to as "spots" hereinafter), to stop the beam when the beam has been irradiated in preset dose to one spot, and to start a next cycle of irradiation as soon as after preparations for the irradiation to the next spot have been finished, followed by repeating the steps of stopping the beam when the beam has been irradiated in preset dose to the next spot and making preparations for the irradiation to the subsequent spot again (see, e.g., Patent Document 2; Japanese Patent No. 2833602). In that case, when a circular accelerator is used, control in the depth direction is performed by successively changing the setting of target energy. More specifically, the affected part in the patient body is divided into a plurality of layers in the direction of depth of the affected part. After the irradiation for all spots in each of the layers is completed, the target energy setting of the circular accelerator is changed and the irradiation is shifted to another layer. In the same layer, the beam is successively irradiated to individual spots by repeating the start and stop of the beam irradiation at the same energy.

SUMMARY OF THE INVENTION

Some of inventors of this application have previously invented and filed a charged particle beam extraction system for performing on/off-control of extraction of an ion beam from a synchrotron during the rotation of the RMW. With that preceding invention, by rotating the RMW such that the ion beam passes through the RMW for a comparatively long time, i.e., over a wider range of RMW rotational angle, the attenuation of the ion beam is varied to a large extent, and hence the SOBP is widened. On the other hand, by rotating the RMW such that the ion beam passes through the RMW for a comparatively short time, i.e., over a narrower range of RMW rotational angle, the attenuation of the ion beam is varied to a small extent, and hence the SOBP is narrowed. Thus, the on/off-control of extraction of the ion beam during the rotation of the RMW enables the SOBP to be produced in various widths by using one RMW. It is therefore possible to reduce the frequency at which the RMW is to be replaced, and to smoothly carry out the treatment for a larger number of patients.

The above-mentioned method of producing the SOBP in various widths using the range modulation wheel and the pencil beam scanning method described above as the related art are expected for advancement of the therapy method using the ion beam because the former is able to ensure smooth treatment and realize a treatment system with a high throughput and the latter is able to increase a degree of dose concentration and realize a treatment system with high irradiation accuracy. Any of those irradiation methods repeats the steps of starting and stopping the irradiation of the ion beam. In the case using a circular accelerator, for example, it is known that, by turning on/off an RF electromagnetic field acting to increase the magnitude of oscillation of charged particles within the separatrix for extraction of the beam, the beam irradiation can be controlled in such a manner as to allow the irradiation during a turned-on period and to stop the irradiation during a turned-off period.

The circular accelerator is operated to cyclically repeat a certain operation pattern made up of an introduction step of introducing ions from a pre-stage accelerator, an acceleration step of accelerating the introduced ions to target energy, an extraction step of extracting the accelerated ions toward the irradiation device, and a deceleration step of decelerating the ions after the end of the extraction step. Therefore, the ion beam is intermittently extracted from the circular accelerator that repeats the operation in such a pattern. The time interval from one extraction of the ion beam to next extraction is called an operation cycle. In the known circular accelerator disclosed in the above-cited Patent Document 1, the operation cycle is fixed, and hence a time of the extraction step during one cycle is also fixed. Accordingly, when the irradiation is performed while repeating the operations of extracting and stopping the beam during the extraction step as in the method of producing the SOBP in various widths using the range modulation wheel and in the pencil beam scanning method, the amount of the ion beam extracted from the circular accelerator toward the irradiation device during one operation cycle is reduced depending on a rate at which the beam extraction time occupies in the extraction step, whereby the irradiation time for one patient is prolonged. As a result, the number of patients treatable per unit time is reduced.

It is an object of the present invention to provide a charged particle beam extraction system and method capable of shortening the irradiation time and increasing the number of patients treatable per unit time.

To achieve the above object, the present invention is featured as follows. When extracting through an irradiation device a charged particle beam extracted from an accelerator which cyclically performs patterned operation including steps of introducing, accelerating and extracting the charged particle beam, control is performed such that when extraction of the charged particle beam is stopped at least once during the extraction step of the accelerator, an amount of the charged particle beam extracted from the accelerator in one cycle is held substantially at a setting value of the amount of extracted beam. With that feature, even when the operations of extracting the beam and stopping the beam extraction are repeatedly executed during the extraction step as in the method of producing various SOBP's using a range modulation wheel (RMW) or in the pencil beam scanning method, the beam amount extracted through irradiation device in one cycle is not reduced. As a result, an irradiation time required for each patient can be shortened, and the number of patients treatable per unit time can be increased.

Preferably, by changing a time of the extraction step of the accelerator, the amount of the charged particle beam extracted from the accelerator in one cycle is held substantially at the setting value.

Preferably, by changing the intensity of the charged particle beam extracted from the accelerator, the amount of the charged particle beam extracted from the accelerator in one cycle is held substantially at a setting value.

According to the present invention, it is possible to shorten the irradiation time and to increase the number of patients treatable per unit time.

BRIEF DESCRIPTION OF THE DRAWINGS

FIGS. 14A-14C are time charts for explaining the advantage of the fourth embodiment.

DESCRIPTION OF THE PREFERRED EMBODIMENTS

Embodiments of a charged particle beam extraction system and method according to the present invention will be described below with reference to the drawings.

First Embodiment

Figure 1:
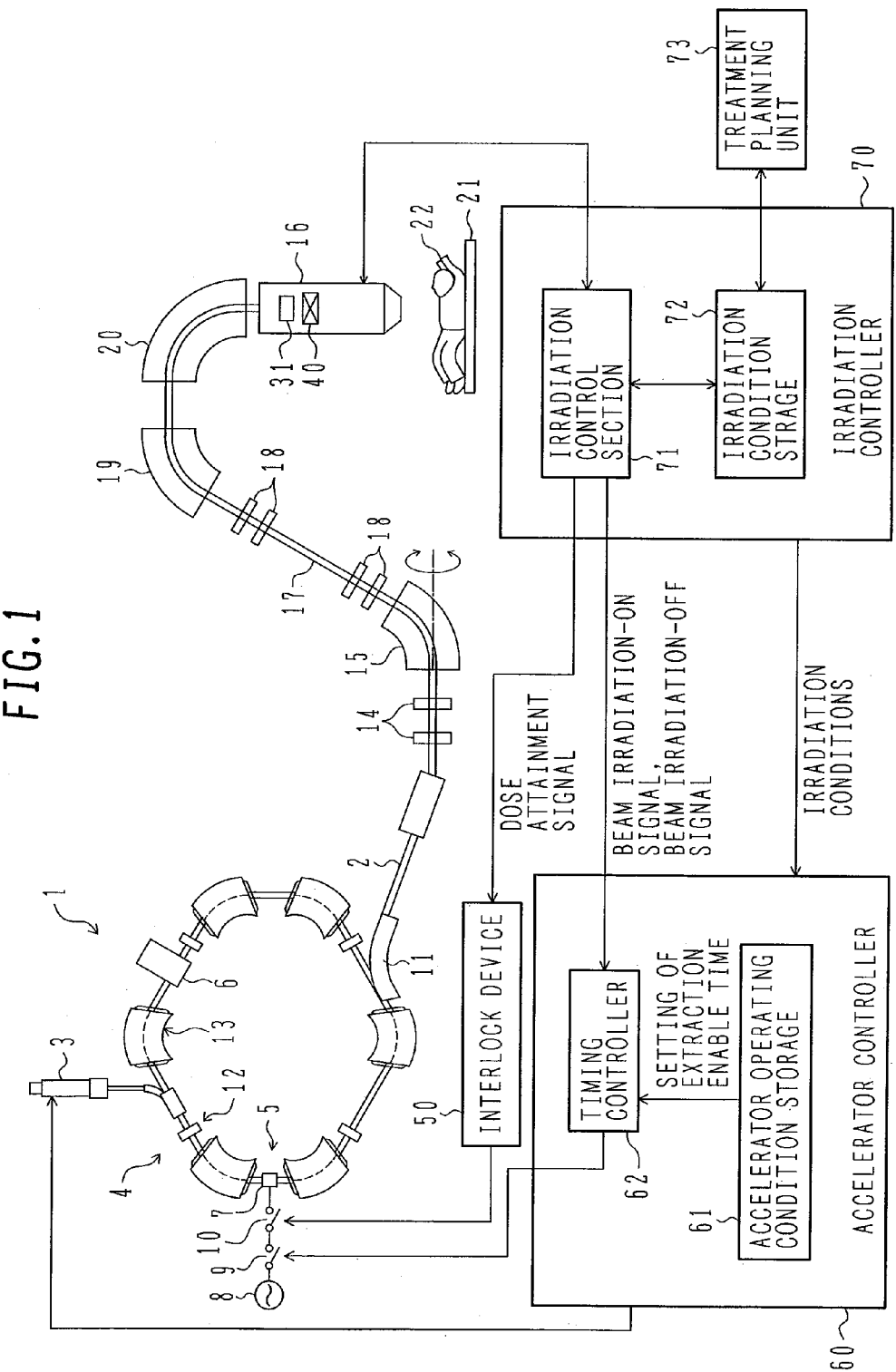
FIG. 1 is a block diagram showing a schematic overall construction of a charged particle beam extraction system according to a first embodiment of the present invention.

A charged particle beam extraction system according to a first preferred embodiment of the present invention will be described below with reference to FIG. 1. The charged particle beam extraction system of this embodiment comprises an ion beam generator 1 and a beam line 2 connected to the downstream side of the ion beam generator 1.

The ion beam generator 1 comprises an ion source (not shown), a pre-stage ion beam generator 3, and a synchrotron (accelerator) 4. The synchrotron 4 includes an RF knockout device 5 and an accelerator 6. The RF knockout device 5 is constituted by connecting an RF knockout electrode 7 disposed in an orbit of a circulating ion beam in the synchrotron 4 and an RF power supply 9 to each other through on/off switches 9, 10. The accelerator 6 comprises an RF cavity (not shown) disposed in the orbit and an RF power supply (not shown) for applying an RF power to the RF cavity. Ions (e.g., protons (or carbon ions)) generated from the ion source are accelerated by the pre-stage ion beam generator 3 (such as a linear ion beam generator). An ion beam extracted from the pre-stage ion beam generator 3 enters the synchrotron 4. The ion beam, i.e., the charged particle beam, is given with energy and accelerated in the synchrotron 4 by the RF power applied from the RF power supply to the ion beam through the RF cavity. After the energy of the ion beam circulating in the synchrotron 4 has been increased to a setting level (e.g., 60 to 250 MeV), an RF wave supplied from an RF power supply 8 for extracting the ion beam is applied to the RF knockout electrode 7 through the on/off switches 9, 10 each being closed, and is then applied to the ion beam from the RF knockout electrode 7. With the application of the RF wave, the ion beam circulating within the separatrix is forced to transit out of the separatrix and to exit from the synchrotron 4 through a beam extraction deflector 11. At the time of extracting the ion beam, currents supplied to quadrupole magnets 12 and bending magnets 13 both disposed in the synchrotron 4 are held at setting current values, and hence the separatrix is also held substantially constant. The extraction of the ion beam from the synchrotron 4 is stopped by opening the on/off switch 9 or 10 to stop the application of the RF power to the RF knockout electrode 7.

The operation of the ion beam generator 1 is controlled by an accelerator controller 60. The accelerator controller 60 comprises an accelerator operating condition storage 61 for storing operating conditions of the synchrotron 4, and a timing controller 62 for executing control related to timing in patterned operation of the synchrotron 4 made up of four steps of introduction, acceleration, extraction and deceleration. Operating conditions of the accelerator corresponding to the irradiation conditions given from an irradiation controller 70 are set in advance through calculations and experiments. Then, the accelerator controller 60 calls the corresponding operating conditions from the accelerator operating condition storage 61 and makes setting of the various components.

The ion beam extracted from the synchrotron 4 is transported to the downstream side through the beam line 2. The beam line 2 includes quadrupole magnets 14 and bending magnets 15 and is connected to a beam passage 17. The beam passage 17 is communicated with the irradiation device 16 disposed in a treatment room and includes quadrupole magnets 18, 18 and bending magnets 19, 20 which are disposed in the beam passage 17 successively from the upstream side in the direction of travel of the ion beam. The ion beam introduced to the beam line 2 is transported to the irradiation device 16 through the beam passage 17 and is then irradiated to the affected part in the body of a patient 22 lying on a treatment bed 21. The components disposed downstream of the bending magnet 15 are installed in an apparatus called a rotating gantry (not shown) which is rotatable about an axis of rotation, as indicated in FIG. 1, around the patient 22 so that the ion beam can be irradiated to the affected part from various directions.

The irradiation device 16 in this embodiment forms an irradiation field by enlarging the irradiation field with a scatterer (not shown) and forming the SOBP (spread-out Bragg peak) with a range modulation wheel (referred to as an "RMW") 40. Inside the irradiation device 16, a dose monitor 31 (not limited to one), the RMW, etc. are arranged on a beam axis.

Figure 2:
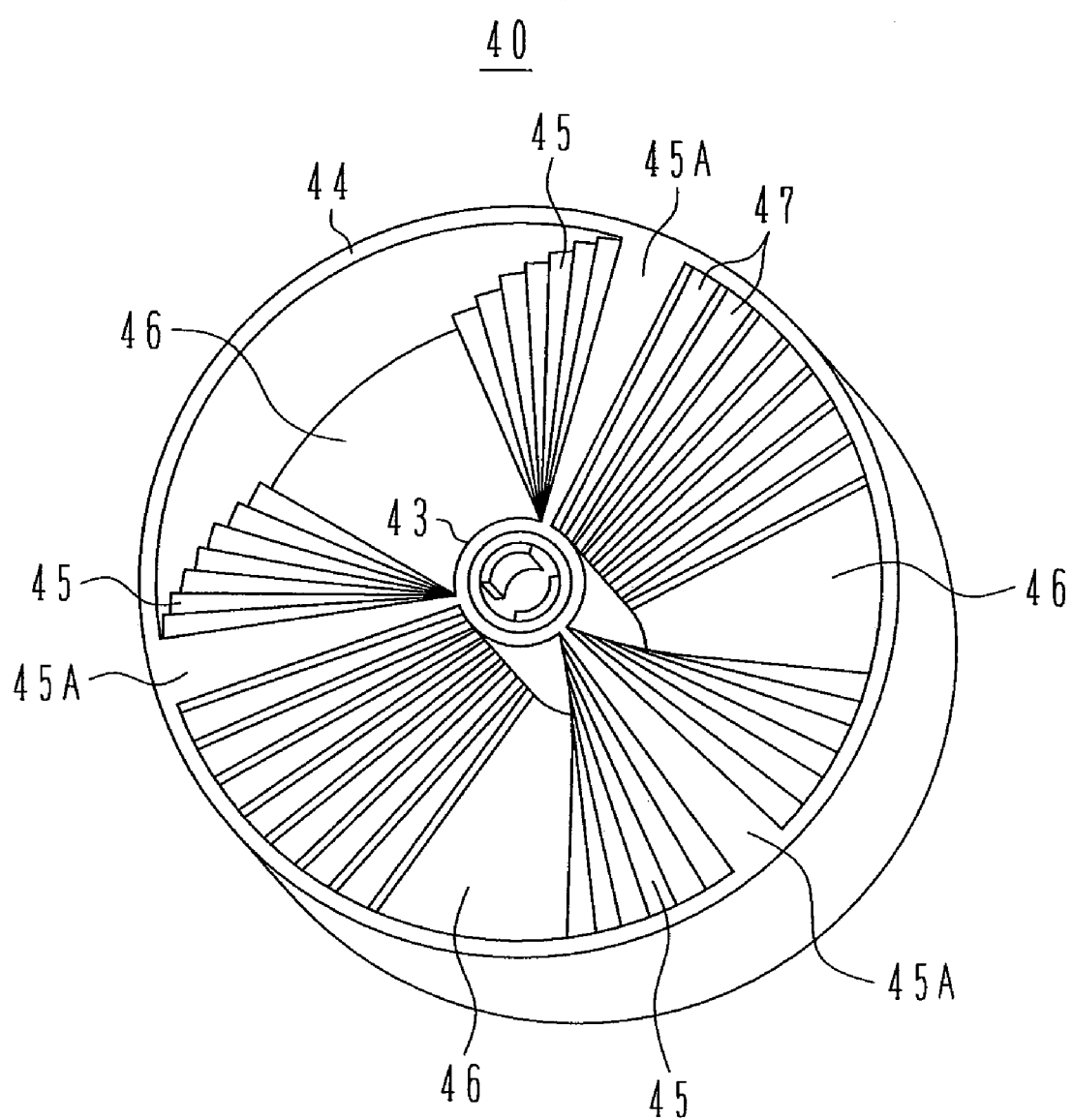
FIG. 2 is a perspective view showing an overall structure of an RMW shown in FIG. 1.

FIG. 2 shows a detailed structure of the RMW 40. As shown in FIG. 2, the RMW 40 comprises a rotary shaft 43, a cylindrical member 44 disposed in concentric relation to the rotary shaft 43, and a plurality of blades 45 (three blades in this embodiment) each of which is mounted to the rotary shaft 43 and is extended in the radial direction of the RMW 40. The blades 45 are each formed to have a circumferential width that increases gradually toward the outer side in the radial direction (namely, the width of each blade is larger in the side nearer to the cylindrical member 44 than in the side nearer to the rotary shaft 43. An outer end of each blade 45 in the radial direction is attached to an inner circumferential surface of the cylindrical member 44. An opening 46 is formed between adjacent two blades 45, 45 in the circumferential direction of the RMW 40. In other words, one unit of the RMW 40 has three openings 46 formed between every two of three blades 45. Each of the openings 46 is also formed such that its circumferential width increases gradually toward the outer side in the radial direction.

Each of the blades 45 has a plurality of plane areas 47 arranged in the form of stairs in the circumferential direction of the RMW 40 (namely, the plane areas 47 correspond to flat surfaces of individual stairs which are stepped by feet). Each of the plane areas 47 has a different thickness relative to a bottom surface of the RMW 40 in the direction of the beam axis (in other words, levels of the plane areas 47 relative to the bottom surface of the RMW 40 differ from one another). The thickness of each plane area 47 is called here the plane area thickness. More specifically, the blade 45 is formed such that the plane area thickness of the blade 45 is increased step by step from each of the plane areas 47 adjacent to the openings 46, which are positioned on both sides of the relevant blade 45 in the circumferential direction, toward the plane area 47 positioned at a top portion 45A of the blade having the largest thickness in the direction of the beam axis. Each plane area 47 is extended from the rotary shaft 43 toward the cylindrical member 44 and has a circumferential width gradually increasing toward the cylindrical member 44.

An angle meter (not shown) is disposed on the thus-constructed RMW 40 to detect a rotational angle (phase in rotation) of the RMW 40. The rotational angle of the RMW 40 detected by the angle meter is outputted to an irradiation control section 71 of the irradiation controller 70.

In the charged particle beam extraction system of this embodiment, a plurality of SOBP's can be formed with one RMW 40 by performing the on/off-control of extraction of the ion beam from the ion beam generator 1 depending on the rotational angle of the RMW 40. That on/off-control of the ion beam extraction will be described in more detail below.

Figure 3:
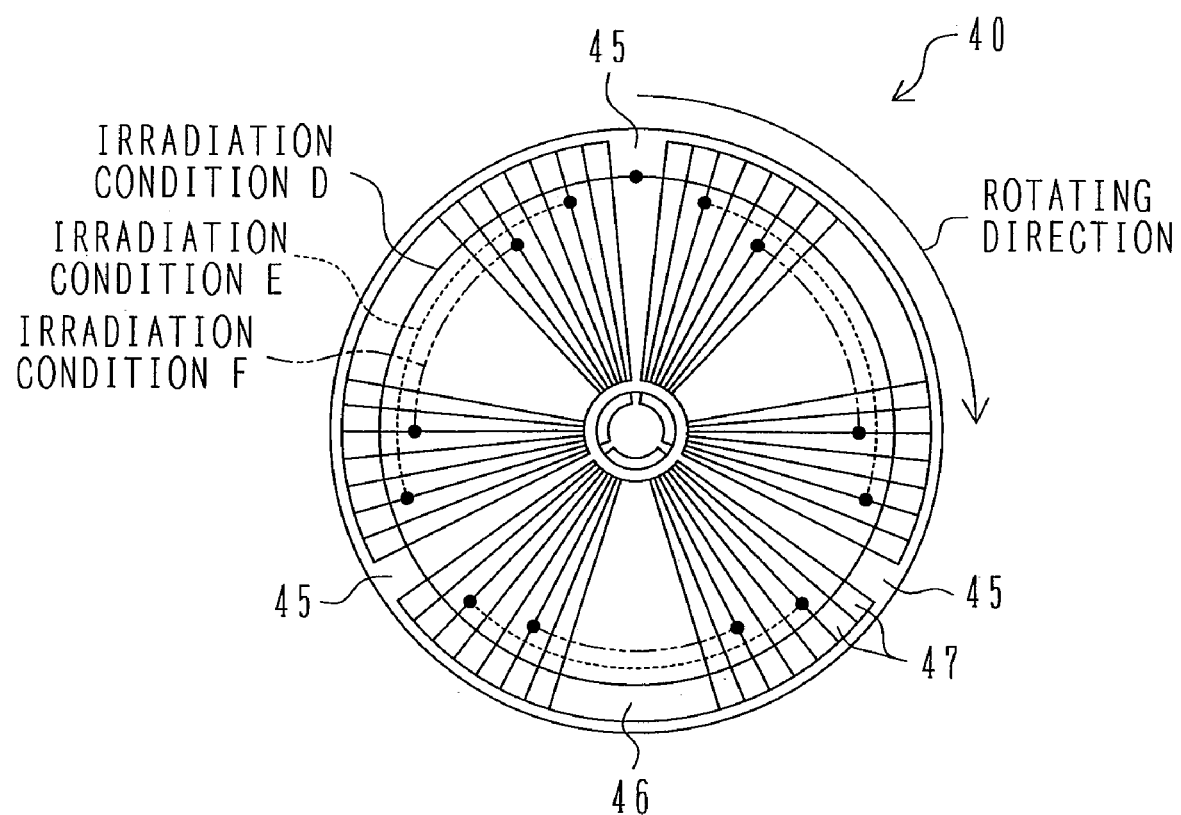
FIG. 3 is a plan view of the RMW shown in FIG. 2, the view showing three kinds of ion beam irradiation conditions.
Figure 4:
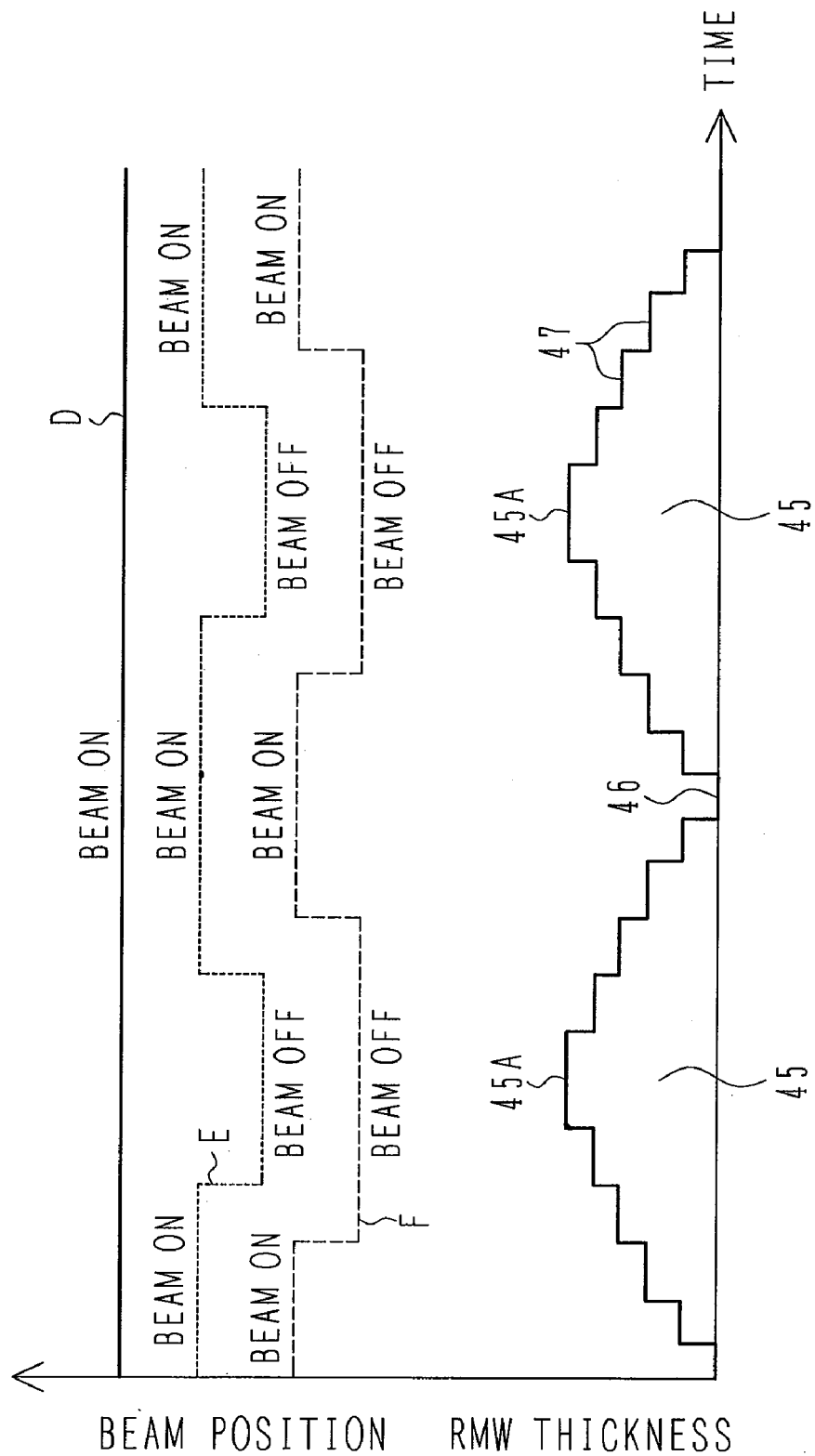
FIG. 4 is a chart showing the three kinds of ion beam irradiation conditions, shown in FIG. 3, on the time serial basis.
Figure 5:
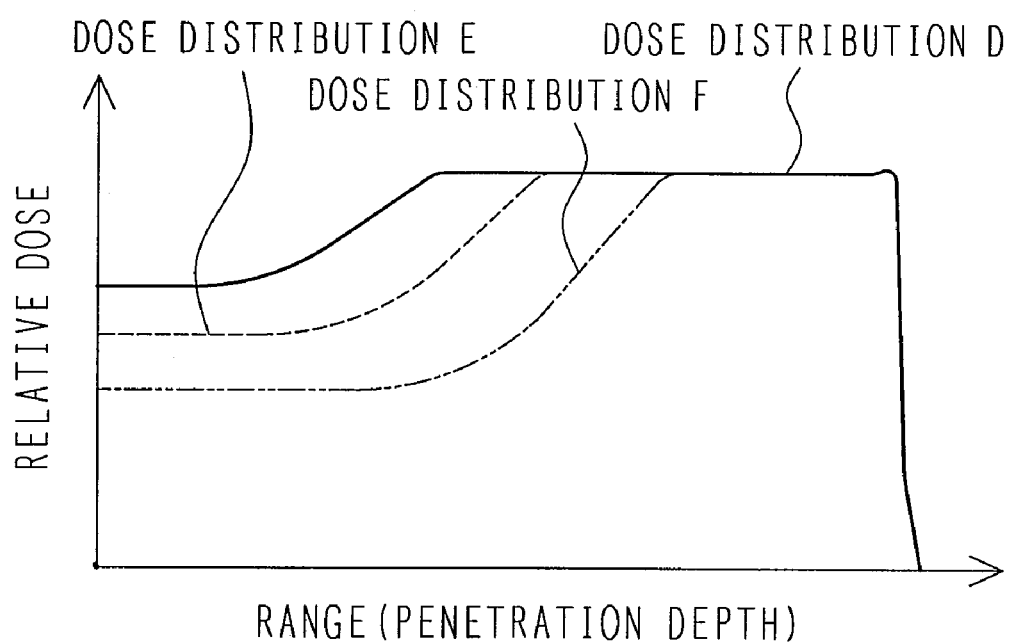
FIG. 5 is a graph showing dose distributions obtained under the three kinds of ion beam irradiation conditions shown in FIG. 3.

FIG. 3 is a plan view of the RMW 40 and shows, by way of example, irradiation conditions D, E and F for three ion beams. FIG. 4 is a chart showing those beam irradiation conditions D, E and F on the time serial basis, and FIG. 5 is a graph showing dose distributions obtained under those beam irradiation conditions D, E and F.

At the time when the ion beam passes the opening 46 of the RMW 40, the beam energy is not attenuated and therefore the Bragg peak is formed in a deep position inside the body. At the time when the ion beam passes the plane area 47 of the blade 45 which has a comparatively thin thickness, the beam energy is slightly attenuated and the Bragg peak is formed substantially in a middle position inside the body. At the time when the ion beam passes the plane area 47 of the blade 45 which has a comparatively thick thickness, the beam energy is largely attenuated and the Bragg peak is formed in a shallow position near the body surface. Accordingly, when the irradiation of the ion beam is always turned on over an entire region of the RMW 40 in the circumferential direction as indicated by the irradiation condition D shown in FIGS. 3 and 4, the above-described change in position of the Bragg peak takes place cyclically with the rotation of the RMW 40. As a result, looking at the dose integrated over time, a comparatively wide SOBP ranging from the position near the body surface to the position deep inside the body is obtained as indicated by the dose distribution D in FIG. 5.

Also, when the irradiation of the ion beam is turned off in the plane area 47 of each blade 45 having a comparatively thick thickness (i.e., near the blade top portion 45A) and the irradiation of the ion beam is turned on in the other circumferential area of the blade 45 as indicated by the irradiation condition E shown in FIGS. 3 and 4, a part of the Bragg peak disappears which is produced with large attenuation of the beam energy and is distributed in a shallow region near the body surface. As a result, a narrower SOBP than that given by the dose distribution D is obtained as indicated by the dose distribution E in FIG. 5.

Further, when the irradiation of the ion beam is turned on in the opening 46 and the plane area 47 of each blade 45 having a comparatively thin thickness and the irradiation of the ion beam is turned off in the other circumferential area of the blade 45 as indicated by the irradiation condition F shown in FIGS. 3 and 4, the beam energy is attenuated to a small extent and the Bragg peak is distributed only in a deep position inside the body. As a result, an even narrower SOBP than that given by the dose distribution E is obtained as indicated by the dose distribution F in FIG. 5. Thus, the charged particle beam extraction system of this embodiment can form a plurality of different SOBP's with one unit of the RMW 40 by performing the on/off-control of extraction of the ion beam depending on the rotational angle of the RMW 40 as described above.

Returning to FIG. 1, the irradiation controller 70 comprises an irradiation control section 71 and an irradiation condition storage 72. A treatment planning unit 73 determines irradiation conditions for the affected part in the body of the patient 22 and stores information of the determined irradiation conditions in the irradiation condition storage 72. Items of the irradiation condition information include data regarding the SOBP to be produced (i.e., the type of the RMW 40 and beam irradiation area information (namely, information representing in which area (rotational angle range) of the RMW 40 the beam is to be turned on/off)). The relations of the SOBP with respect to the type of the RMM 40 and the beam irradiation area information are determined in advance through calculations, experiments, etc.

The irradiation control section 71 executes the on/off-control of extraction of the ion beam from the ion beam generator 1 to form the SOBP as intended. More specifically, the irradiation control section 71 first reads SOBP data (beam irradiation area information) from among the irradiation condition information stored in the irradiation condition storage 72. Then, the irradiation control section 71 receives the rotational angle of the RMW 40 from the angle meter and outputs, in accordance with the beam irradiation area information read out of the irradiation condition storage 72, a beam irradiation-on signal to the timing controller 62 in the accelerator controller 60 when the rotational angle of the RMW 40 reaches the angle corresponding to the beam-on area.

Figure 6:
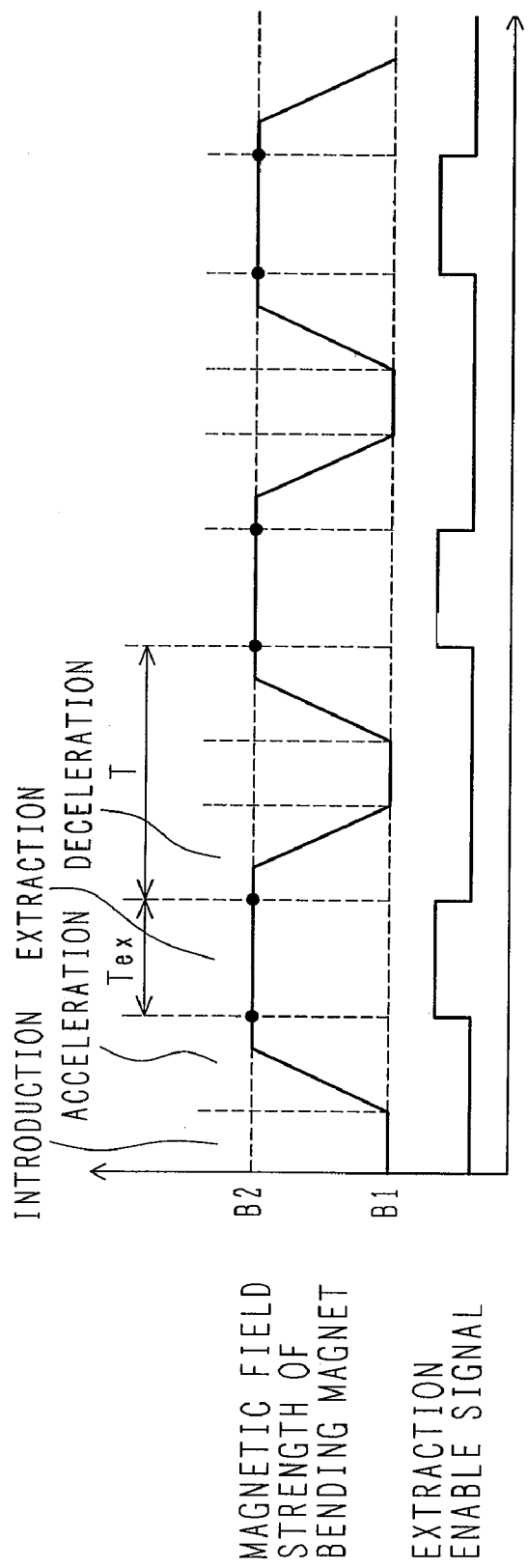
FIG. 6 is a chart showing a basic operation pattern for a synchrotron shown in FIG. 1.

On the other hand, as shown in FIG. 6, the synchrotron 4 is operated while cyclically repeating patterned operation made up of four steps of introduction, acceleration, extraction and deceleration. In the chart of FIG. 6, the horizontal axis indicates time, and the vertical axis indicates the intensity of a magnetic field generated by the bending magnet 13, which represents the operation pattern of the synchrotron 4. Note that the intensity of the magnetic field generated by the bending magnet 13 indicated in FIG. 6 represents the case where the beam is always extracted during the extraction step without performing the on/off-control of extraction of the ion beam. In FIG. 6, B1 corresponds to the intensity of the magnetic field for circulating ions at energy when the ions are introduced, and B2 corresponds to the intensity of the magnetic field for circulating ions at energy after acceleration of the ions. Further, Tex indicates an extraction enable time (extraction step time) per cycle, T indicates a time from termination of the beam extraction in one cycle to start of the beam extraction in a next cycle, and (Tex+T) indicates one operation cycle of the synchrotron 4.

In the extraction step, an extraction enable signal is outputted from a magnet power-supply controller (not shown) to the timing controller 62 in the accelerator controller 60. The on/off timing of the extraction enable signal is also shown in FIG. 6 along with changes in the intensity of the magnetic field generated by the bending magnet 13. At the timing when the on-duration of the extraction enable signal received from the magnet power-supply controller is overlapped with the duration of the beam irradiation-on signal received from the irradiation control section 71 of the irradiation controller 70, the timing controller 62 closes the on/off switch (i.e., an amount-of-extracted beam adjusting unit or an extraction time adjusting unit) 9 to extract the ion beam from the synchrotron 4.

Also, the timing controller 62 has an integrating timer (not shown) for the beam irradiation-on/off signal and integrates the turned-on time of the beam irradiation signal outputted from the irradiation control section 71. On the other hand, the timing controller 62 sets the extraction enable time in accordance with the information regarding the accelerator operating conditions, which is read out of the accelerator operating condition storage 61 corresponding to the irradiation conditions inputted from the irradiation controller 70 (as described in more detail later). Then, when the integrated time of the beam irradiation-on signal outputted from the irradiation control section 71 reaches the set extraction enable time, the on/off switch 9 is opened to stop the extraction of the ion beam from the synchrotron 4.

Figure 7:
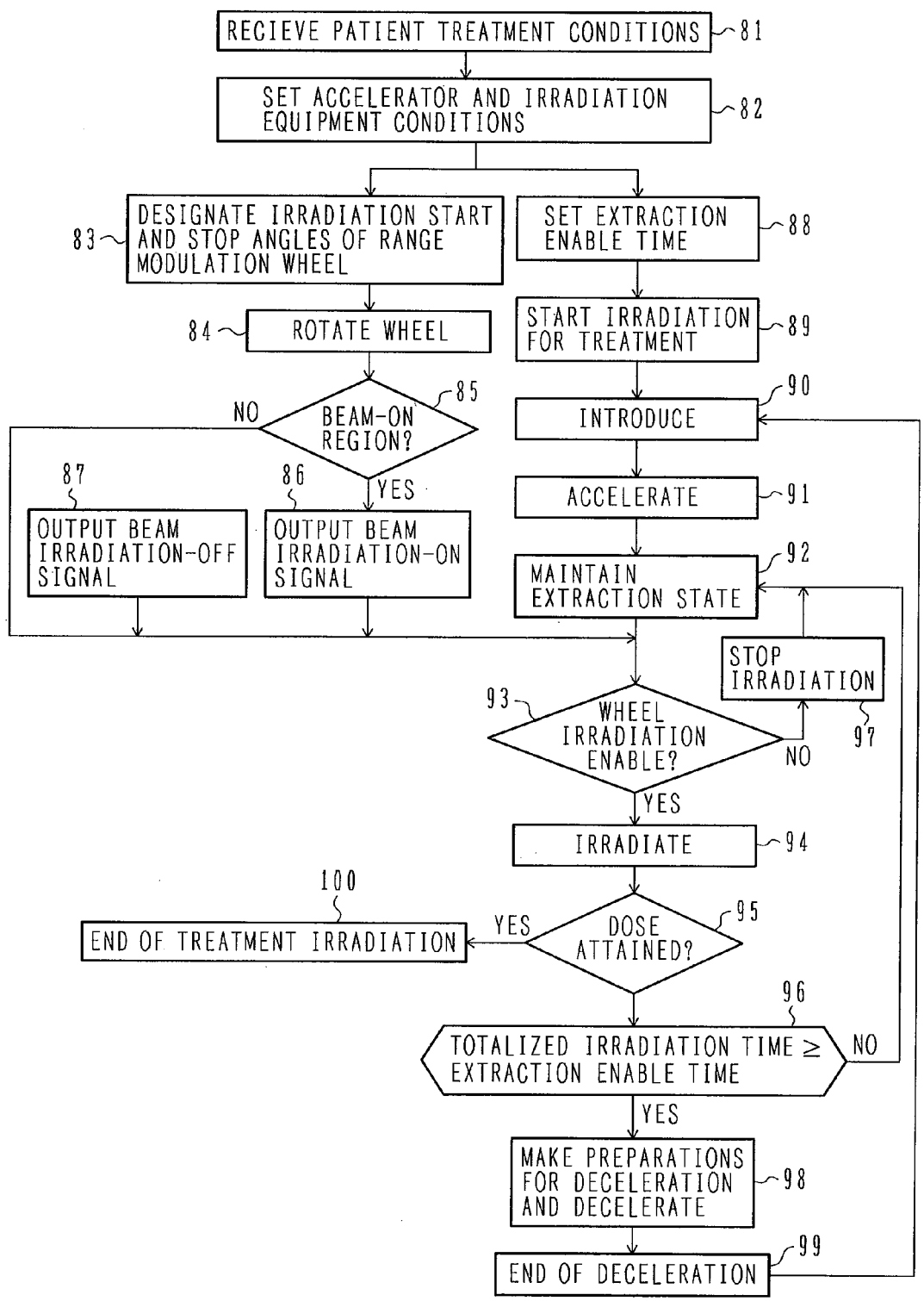
FIG. 7 is a flowchart showing beam irradiation steps executed in the charged particle beam extraction system according to the first embodiment of the present invention.

Steps of treatment irradiation performed in the thus-constructed charged particle beam extraction system of this embodiment will be described below with reference to FIG. 7. The steps shown in a flowchart of FIG. 7 are executed by the accelerator controller 60 and the irradiation controller 70. The execution of those steps realizes control to hold the amount of the ion beam extracted from the synchrotron 4 in one cycle substantially at a setting value, i.e., to hold the amount of the extracted ion beam substantially constant.

First, the irradiation controller 70 inputs and stores, in the irradiation condition storage 72, the irradiation conditions (such as the beam energy and the SOBP) for the affected part in the body of the patient 22, which have been determined by the treatment planning unit 73 (step 81). Then, the irradiation control section 71 of the irradiation controller 70 sets the operating conditions of the various components of the irradiation device 16 in accordance with the stored irradiation conditions. Further, the accelerator controller 60 receives the irradiation conditions from the irradiation controller 70 and sets the operating conditions of the various components of the ion beam generator 1 (step 82).

The irradiation control section 71 of the irradiation controller 70 reads, out of the irradiation condition storage 72, the beam irradiation area information (i.e., the irradiation start angle and the irradiation stop angle for the RMW 40) contained in the SOBP data stored as the irradiation conditions (step 83). Then, the irradiation control section 71 outputs a drive signal to a driving unit (not shown) for the RMW 40, which is disposed in the irradiation device 16, thereby rotating the RMW 40 (step 84). During the rotation of the RMW 40, the irradiation control section 71 always receives the rotational angle of the RMW 40 from the angle meter and determines whether the received rotational angle is matched with the irradiation start angle of the RMW 40 (step 85). If both the angles are matched with each other, the irradiation control section 71 outputs the beam irradiation-on signal to the timing controller 62 in the accelerator controller 60 (step 86). On the other hand, if the rotational angle of the RMW 40 received from the angle meter is matched with the irradiation stop angle, the irradiation control section 71 outputs the beam irradiation-off signal to the timing controller 62 in the accelerator controller 60 (step 87). By repeating the above-described steps, the beam on/off-control is performed depending on the rotational angle of the RMW 40.

In parallel to the above-described steps 83-87, the timing controller 62 in the accelerator controller 60 sets the extraction enable time (step 88) based on the irradiation conditions and the operating conditions which have been received and set in step 82. A practical manner of setting the extraction enable time will be described below with reference to FIG. 8.

Figure 8:
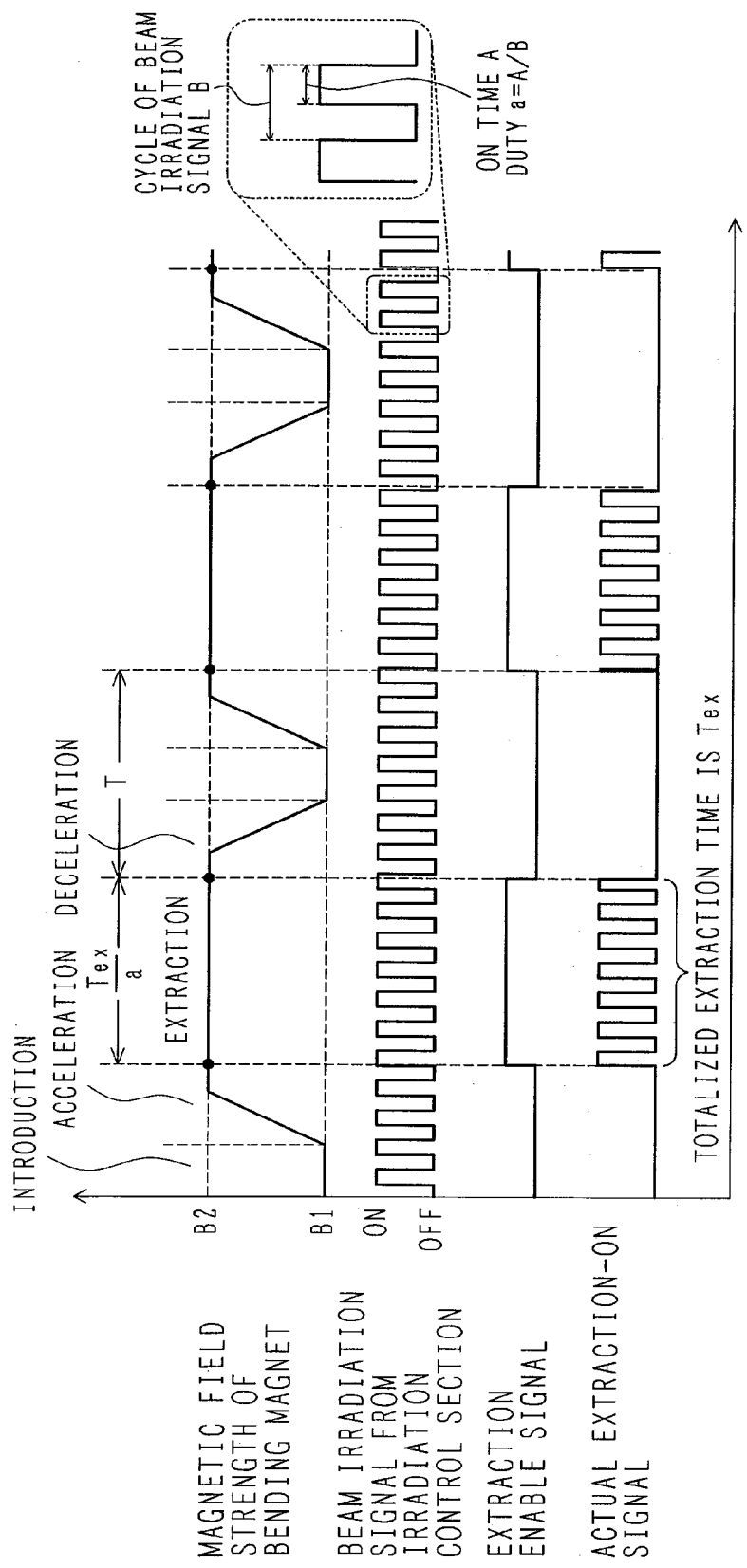
FIG. 8 is a chart showing an operation pattern for the synchrotron, shown in FIG. 1, in which an extraction time is prolonged in accordance with a rate of a beam-on time in the extraction step.

As shown in FIG. 8, a ratio of the turned-on time to the time of one cycle (referred to as a "duty" hereinafter) of the beam irradiation signal outputted from the irradiation control section 71 to the timing controller 62 is assumed to be a (=A/B). For the sake of simplicity of explanation, the beam irradiation signal is assumed to have a waveform repeated such that the turned-on time is A and the time of one cycle is B. Accordingly, the duty a can also be said as a rate of the beam extraction-on time during the extraction step of the synchrotron 4. For example, when the beam is not turned on/off during the rotation of the RMW 40 as with the irradiation condition D shown in FIGS. 3 and 4, the duty a=1 is resulted. Also, when the SOBP is to be narrowed as with the irradiation conditions E, F shown in FIGS. 3 and 4, the duty a is smaller than 1. In other words, the duty is in the range of $0 < a \leq 1$. The timing controller 62 receives the irradiation start angle and the irradiation stop angle for the RMW 40, which are contained in the SOBP data stored as the irradiation conditions, and computes the duty a from the received information. Then, the timing controller 62 sets the time of the extraction step during one cycle (i.e., the time from the start of the irradiation to the termination of the irradiation) to Tex/a so that the integrated time during which the beam has been actually extracted becomes the extraction enable time Tex (see FIG. 6). As a result, it is ensured that the integrated time of the beam irradiation-on signal (indicated by "actual extraction-on signal" in FIG. 8) is equal to the extraction enable time Tex, the beam irradiation-on signal being outputted from the timing controller 62 to the on/off switch 9 at the timing when the on-duration of the extraction enable signal received from the magnet power-supply controller is overlapped with the duration of the beam irradiation-on signal received from the irradiation control section 71.

Returning to FIG. 7, when an operator depresses a treatment start button disposed, for example, on a console (not shown), the treatment irradiation is started (step 89). First, the accelerator controller 60 outputs an extraction start signal to the pre-stage ion beam generator 3. Responsively, the ion beam extracted from the pre-stage ion beam generator 3 is introduced to the synchrotron 4 (step 90). At this time, the excitation currents for the various magnets in the synchrotron 4 are controlled to respective values corresponding to the incident energy of the ion beam by the magnet power-supply controller (not shown). Then, while gradually increasing the excitation currents for the various magnets in the synchrotron 4, the ion beam circulating in the synchrotron 4 is accelerated by the RF power applied to the ion beam from the RF power supply through the RF cavity (step 91). When the energy of the ion beam is increased to a preset level, the excitation currents supplied to the various magnets are held at respective constant setting values (step 92). At this time, the extraction enable signal is outputted to the timing controller 62 from the magnet power-supply controller (not shown).

Next, the timing controller 62 in the accelerator controller 60 determines whether the beam irradiation-on signal is inputted from the irradiation control section 71 of the irradiation controller 70 (step 93). If the beam irradiation-on signal is outputted to the timing controller 62 in the above-described step 86, the beam irradiation-on signal is outputted to the on/off switch 9, thereby closing the on/off switch 9. Responsively, the RF wave supplied from the RF power supply 8 for extracting the ion beam is applied to the RF knockout electrode 7 through the closed on/off switches 9, 10 (the on/off switch 10 being assumed to be now closed), and is then applied to the ion beam from the RF knockout electrode 7. With the application of the RF wave, the ion beam circulating within the separatrix is forced to transit out of the separatrix and to exit from the synchrotron 4 through the extraction deflector 11. The ion beam extracted from the synchrotron 4 is transported through the beam line 2 to the irradiation device 16 on the downstream side and is then irradiated to the affected part in the body of a patient 22 lying on the treatment bed 21 (step 94).

During the irradiation, the irradiation control section 71 of the irradiation controller 70 always receives the detected value of dose of the irradiated ion beam from the dose monitor 31 and integrates the detected dose value. Then, the irradiation control section 71 determines whether the integrated dose value reaches a dose limit value required for the treatment irradiation to the patient 22, which has been set by the treatment planning unit 73 (step 95).

Meanwhile, the timing controller 62 in the accelerator controller 60 integrates the turned-on time of the beam irradiation signal inputted from the irradiation control section 71 of the irradiation controller 70 and determines whether the integrated time reaches the extraction enable time set in the above-described step 88 (step 96). If the integrated time of the beam irradiation-on signal does not yet reach the extraction enable time, the processing of steps 92-96 is repeated. During the repeated processing, if the beam irradiation-off signal is inputted to the timing controller 62 from the irradiation control section 71 of the irradiation controller 70 in the above-described step 87, the beam irradiation-off signal is outputted to the on/off switch 9, thereby opening the on/off switch 9. Responsively, the beam extraction from the synchrotron 4 is stopped (step 97). Also, if the beam irradiation-on signal is inputted again to the timing controller 62 from the irradiation control section 71, the beam irradiation-on signal is outputted to the on/off switch 9, thereby closing the on/off switch 9 to start the beam extraction from the synchrotron 4 again.

If the integrated time of the beam irradiation-on signal inputted from the irradiation control section 71 reaches the extraction enable time with the repetition of steps 92-97, the beam irradiation-off signal is immediately outputted to the on/off switch 9, thereby stopping the beam extraction from the synchrotron 4. Then, the RF power applied to the ion beam from the RF power supply through the RF cavity is reduced while gradually decreasing the excitation currents for the various magnets in the synchrotron 4 under control of the magnet power-supply controller (not shown), whereby the ion beam is decelerated (step 98). After the end of the deceleration (step 99), the excitation currents for the various magnets in the synchrotron 4 are set again to the respective values corresponding to the incident energy of the ion beam by the magnet power-supply controller (not shown) so that the ion beam extracted from the pre-stage ion beam generator 3 is introduced to the synchrotron 4 again. In this way, the control process advances to the operation pattern for the next cycle, followed by repeating the steps 90-99.

If the dose limit is detected during the process of repeating the steps 90-99, the irradiation control section 71 outputs a dose attainment signal to an interlock device 50. Responsively, the interlock device 50 outputs the beam irradiation-off signal to the on/off switch 10, thereby opening the on/off switch 10. As a result, the beam extraction from the synchrotron 4 is stopped and the treatment irradiation is terminated (step 100).

In this embodiment, as described above, the on/off switches and signal paths for operating the on/off switches are designed to constitute separate lines for the beam-on/off control executed by the timing controller 62 and the beam-off control executed by the interlock device 50 upon the detection of the dose limit for the purpose of ensuring safety. However, those on/off switches and signal paths may be integrated into one line.

The timing controller 62 functions as an extraction enable time setting unit for setting an extraction enable time of a charged particle beam, an integrating unit for integrating a time during which the charged particle beam has been extracted, a determining unit for determining whether an extraction time has reached the extraction enable time, and an extraction stopping unit for stopping the extraction of the charged particle beam.

With the charged particle beam extraction system of this embodiment, the following advantages are obtained.

In the charged particle beam extraction system of this embodiment, the time of the extraction step during one cycle (i.e., the time from the start of the irradiation to the termination of the irradiation) is set to Tex/a. By so prolonging the time of the extraction step depending on the duty a, even when the operations of extracting the beam and stopping the extraction are repeatedly performed during the extraction step, the integrated time during which the beam has been actually extracted can be made substantially equal to the extraction enable time Tex resulting when the beam-off control is not performed during the extraction step. As a result, even when the operations of repeatedly extracting the beam and stopping the extraction are performed to obtain various widths of the SOBP by using the RMW 40 as in this embodiment, the amount of the beam extracted from the synchrotron 4 in one cycle can be held substantially at the setting value without being reduced. Namely, the beam amount extracted in one cycle can be held substantially constant. Because the total dose required for the treatment irradiation to the patient 22 is decided before starting the treatment, the number of operation cycles of the synchrotron 4 in each plan of treatment irradiation can be reduced and the irradiation time can be cut. It is hence possible to increase the number of patient treatable per unit time.

Further, with this embodiment, the dose rate of the charged particle beam extraction system can be increased. This effect of increasing the dose rate is increased as the duty a represented by the rate of the beam irradiation-on signal during the extraction step decreases. This point will be described below.

The dose rate applied to the affected part in the patient body per cycle of treatment irradiation can be expressed by the following formula (1) using the amount of ions (charged particles) obtained from the synchrotron 4 per cycle and the time of one cycle on condition of the cycle being constant:

$$(\text{dose rate}) \propto (\text{amount of charged particles per cycle}) / (\text{time of one cycle}) \quad (1)$$

In this embodiment, a dose rate $D_1$ can be expressed by the following formula (2) using a proportional coefficient K on an assumption that the number of ions per cycle is Q [number of particles/cycle], the extraction enable time is Tex, and the time required for the deceleration, introduction and acceleration steps other than the extraction step is T. The proportional coefficient K is a numerical value depending on the spread-out size of the irradiation field, the energy of the ion beam, etc. and it takes the same value when the irradiation conditions except for the SOBP are the same.

$$D_1 = K \frac{Q}{T + \frac{T_{ex}}{a}} \quad (2)$$

For comparison, assuming the case where the operating method of setting the extraction enable time depending on the duty a, which is given as the turned-on time of the beam irradiation signal, and performing the beam extraction until reaching the set time is not employed unlike this embodiment, the amount of the beam extracted per cycle is reduced to aQ corresponding to the duty a. Accordingly, a dose rate $D_0$ in the comparative case is expressed by the following formula (3):

$$D_0 = K \frac{aQ}{T + T_{ex}} \quad (3)$$

An increase of the dose rate obtained with the operating method according to this embodiment is given as a dose rate ratio of $D_1/D_0$ and expressed by the following formulae (4):

$$\frac{D_1}{D_0} = \frac{Q}{T + \frac{T_{ex}}{a}} \cdot \frac{T + T_{ex}}{aQ} = \frac{T + T_{ex}}{aT + T_{ex}} \quad (4)$$

Figure 9:
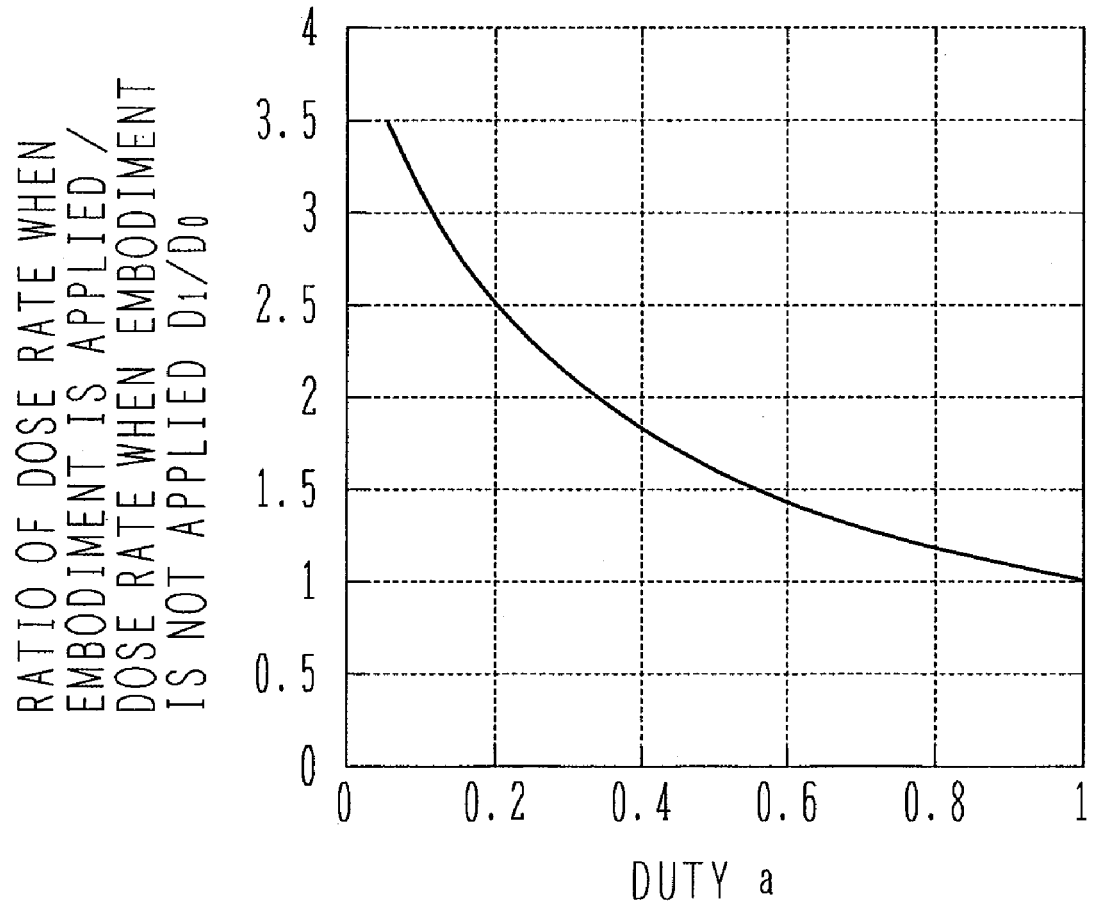
FIG. 9 is a graph for explaining a dose rate increasing effect obtained with the first embodiment of the present invention.

FIG. 9 shows the dependency of $D_1/D_0$ upon the duty a on an assumption of, by way of example, that the extraction enable time is 0.5 sec and the time required for the deceleration, introduction and acceleration steps other than the extraction step is 1.5 sec. As seen from FIG. 9, the smaller the duty a, the larger is the dose rate ratio and the higher is the effect of the operating method according to this embodiment.

Still other effects of this embodiment are as follows. As seen from FIG. 8 described above, corresponding to the extended operation cycle of the synchrotron 4, the number of times of turning on/off the beam depending on the rotational angle of the RMW 40 per operation cycle can be increased.

Also, it is possible to reduce the number of irradiation steps being shorter than the actually required turned-on time, which may occur in extraction start and termination stages during the extraction step per cycle. This results in such an advantage that, when the dose distribution in the depth direction is obtained in the form averaged over time as shown in FIG. 5, the time required for the averaging can be shortened.

If the duty a is very small, the time of the extraction step (i.e., the time from the start to termination of the extraction) is extended to such an extent as raising a risk that the quality of the charged particle beam may change because the number of circulations of the accelerated charged particles in the synchrotron 4 is greatly increased. In view of such a risk, the control may be executed through the steps of setting an upper limit value for the time from the start to termination of the extraction, and stopping the extraction of the beam for a shift to the deceleration step when the extraction step time exceeds the upper limit value. The upper limit value is determined in advance through calculations and experiments to be employed for each of the operating conditions of the accelerator or all the operating conditions.

Figure 10:
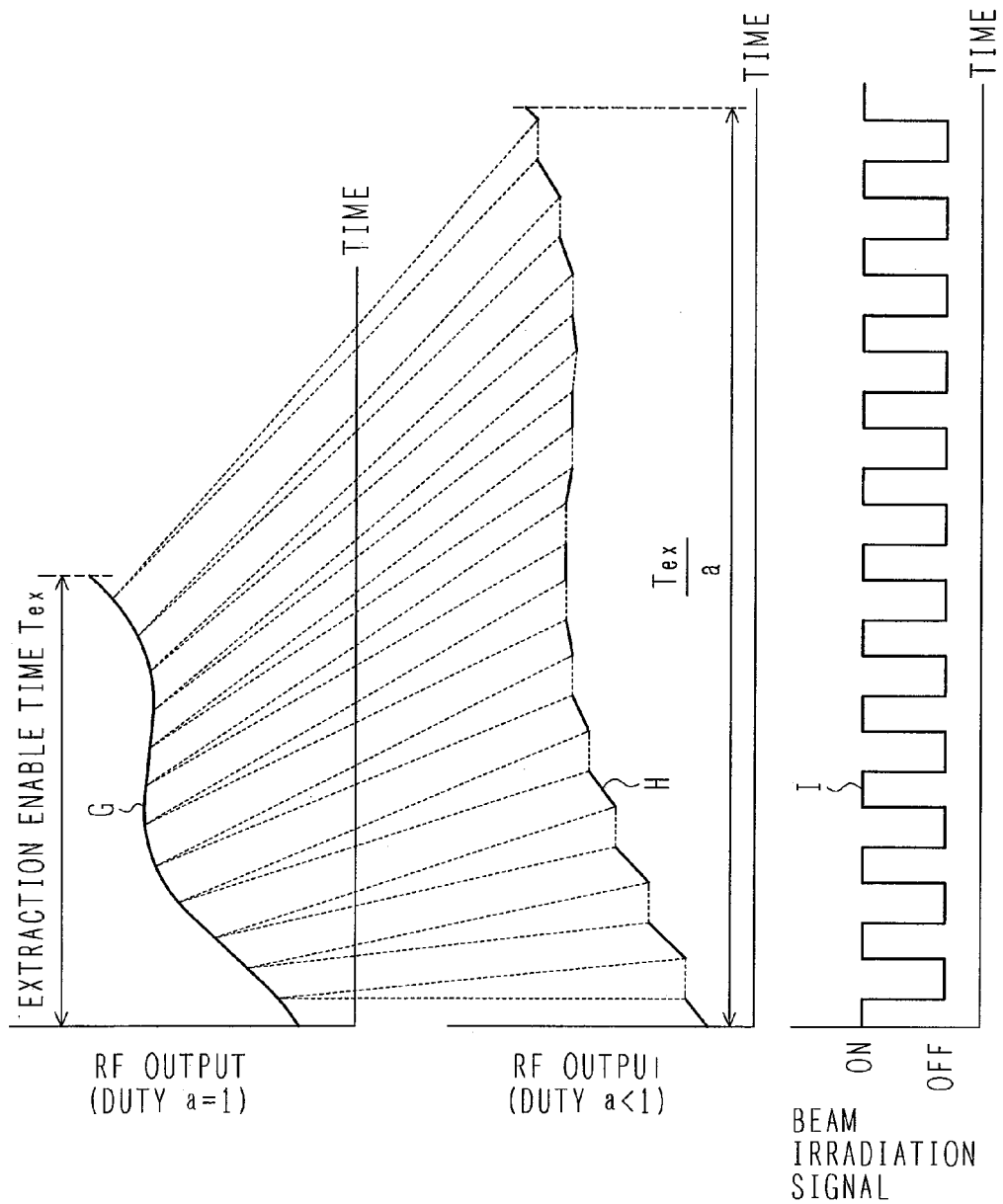
FIG. 10 is a set of charts showing one example of time-dependent changes of an RF output applied to an RF electrode for extraction when an ion beam obtained from the synchrotron is changed with time.

When the amount of the ion beam extracted from the synchrotron 4 per cycle is greatly varied with time, the RF power supply may be controlled by an RF output controller 63 (see FIG. 11, etc.) such that the RF output applied to the RF knockout electrode 7 during the beam extraction is changed with time as indicated, for example, by G in FIG. 10. This is based on such a property that the intensity of the ion beam extracted from the synchrotron 4 per unit time can be changed to increase or decrease depending on the intensity of the RF output. Further, in the case of changing the RF output in such a pattern, when the beam-on/off control is executed depending on the rotational angle of the RMW 40 as in the first embodiment, it is preferable to stop update of the RF output pattern during the beam-off time (i.e., keep the RF output constant) and to update the RF output pattern (i.e., change the RF output) during only the beam-on time, thereby providing an RF output pattern as indicated, for example, by H in FIG. 10. As a result, in spite of the duty a being changed, the waveform of the RF output can be held constant (except for the beam-off time), and therefore the amount of the ion beam extracted from the synchrotron 4 per cycle can be held substantially at the setting value.

Further, to keep constant the amount of the ion beam extracted per cycle, the first embodiment described above takes steps of integrating the output time of the beam irradiation-on signal from the irradiation control section 71 of the irradiation controller 70, continuing the irradiation if the integrated time is within the extraction enable time, and stopping the irradiation for shifting the synchrotron 4 to the deceleration step if the integrated time exceeds the extraction enable time. However, the manner of keeping constant the amount of the ion beam is not limited to the above-described one. As an alternative, the method may comprise, for example, the steps of presetting, in the irradiation control section 71, a dose output value corresponding to the amount of the ion beam to be extracted per cycle, which is measured by the dose monitor 31 shown in FIG. 1, continuing the irradiation if the integrated dose value detected per cycle is within the preset output value, and stopping the irradiation for a shift to the deceleration step if the detected dose value exceeds the preset output value.

Moreover, in the first embodiment, the output time of the beam irradiation-on signal is integrated in the accelerator controller 60. However, the manner of integrating the output time of the beam irradiation-on signal is not limited to that one and may be executed through the steps of outputting the extraction enable time set by the accelerator controller 60 to the irradiation controller 70, and executing integration of the irradiation-on time per cycle and determination on a shift to the deceleration step in the irradiation controller 70.

Second Embodiment

Figure 11:
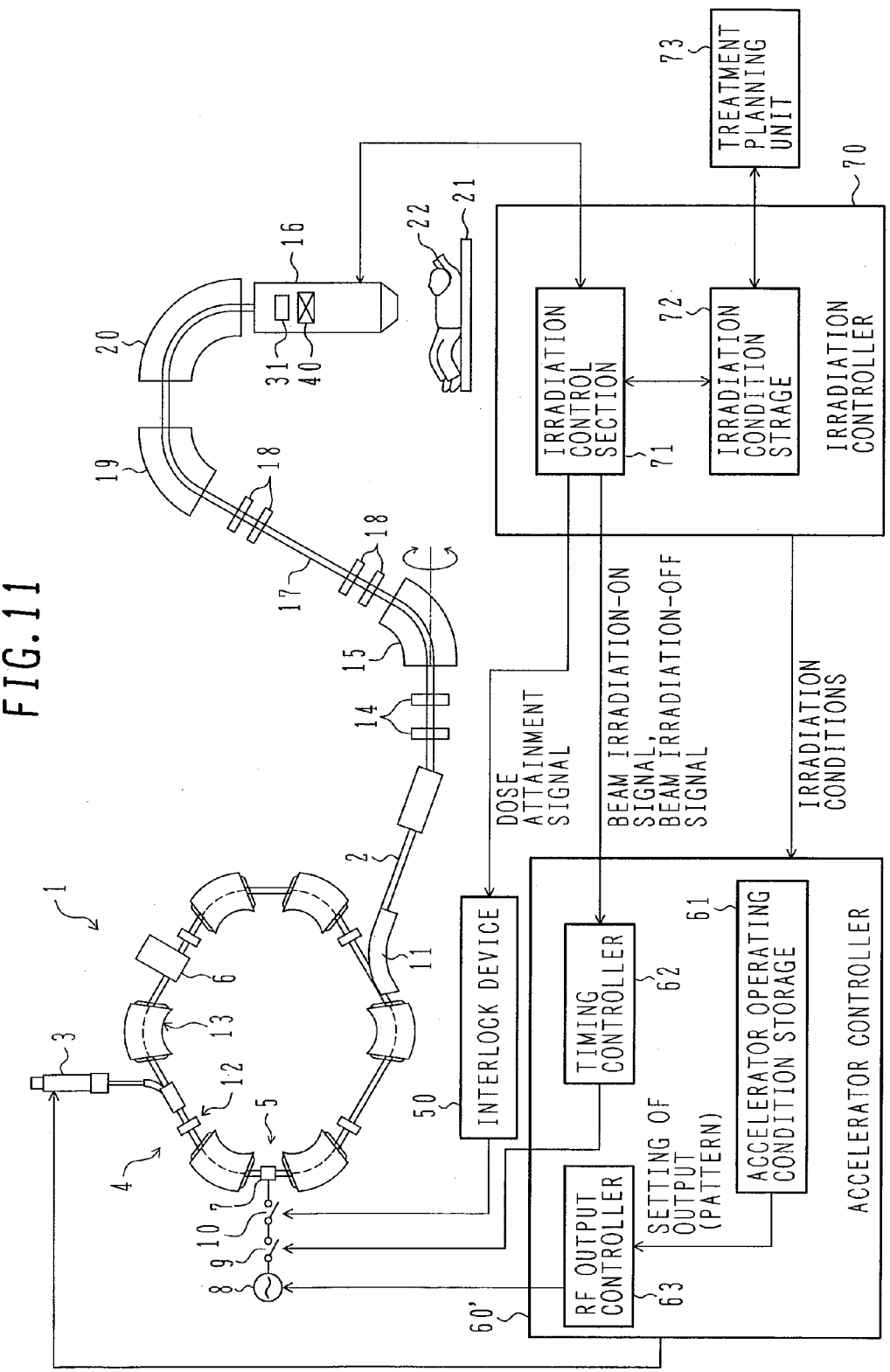
FIG. 11 is a block diagram showing a schematic overall construction of a charged particle beam extraction system according to a second embodiment of the present invention.

A charged particle beam extraction system according to another preferred embodiment of the present invention will be described below as a second embodiment with reference to FIG. 11.

The charged particle beam extraction system of this embodiment has an accelerator controller 60' including an RF output controller 63 for controlling an output of RF power from an RF power supply (amount-of-extracted beam adjusting unit or beam intensity adjusting unit) 8. More specifically, in the synchrotron 4, the amount of an ion beam capable of being accelerated and extracted per cycle can be held substantially constant in each cycle, and the extraction enable time (extraction step time) Tex per cycle is decided depending on a contribution of an RF electromagnetic field for beam extraction, which is applied to an RF knockout electrode 7, to ions circulating in the synchrotron 4. That contribution is decided depending on energy of the circulating ion beam and the output of the RF power supply 8, which decides the power of the RF electromagnetic field. The relationship between the extraction enable time and the output of the RF power supply 8 can be determined in advance through calculations and experiments. Accordingly, when the extraction enable time (extraction step time) Tex per cycle is set constant, the amount of the ion beam extracted from the synchrotron 4 per cycle can be controlled by controlling the output of the RF power supply 8 with the RF output controller 63. This embodiment is intended to execute such operation control.

As described above, the SOBP data stored as the irradiation conditions in the irradiation condition storage 72 of the irradiation controller 70 contains the type of the RMW 40 and the beam irradiation area information (namely, information representing in which area (rotational angle range) of the RMW 40 the beam is to be turned on/off)). The relations of the SOBP with respect to the type of the RMW 40 and the beam irradiation area information are determined in advance through calculations, experiments, etc. In this embodiment, the RF output controller 63 computes the duty a, i.e., the turned-on time of the beam irradiation signal, based on irradiation start angle information and irradiation stop angle information for the RMW 40, which are contained in the irradiation conditions (alternatively, as in the first embodiment, the duty a may be computed by the timing controller 62 and inputted to the RF output controller 63). In accordance with the computed duty a, the RF output controller 63 executes control to increase the output of the RF power supply 8, which is applied to the RF knockout electrode 7, so that the amount of the ion beam extracted per cycle is substantially constant. At this time, the operation cycle of the synchrotron 4 is controlled by the timing controller 62 to be held constant regardless of the beam-on/off operation.

In the foregoing description, the RF output controller 63 constitutes a control unit stated in each claim, and also constitutes a beam intensity setting unit for setting the intensity of a charged particle beam and further constitutes an RF output control unit for controlling an RF output applied to the charged particle beam.

With the above-described charged particle beam extraction system of this embodiment, the output of the RF power supply 8 applied to the RF knockout electrode 7 is controlled to increase depending on the duty a. Therefore, even when the operations of extracting the beam and stopping the extraction are repeatedly performed during the extraction step, the amount of the beam extracted from the synchrotron 4 in one cycle can be held substantially at a setting value without causing a reduction of the beam amount. Accordingly, the irradiation time can be cut as in the first embodiment. As a result, the number of patients treatable per unit time can be increased.

Further, this embodiment can also increase the dose rate of the charged particle beam extraction system. More specifically, in the irradiation executed in this embodiment, the operation cycle of the synchrotron 4 is (T+Tex) and the amount of the extracted ion beam is Q, whereby a dose rate $D_2$ is expressed by the following formula (5):

$$D_2 = K \frac{Q}{T+T_{ex}} \quad (5)$$

A ratio $D_2/D_0$ of the dose rate $D_2$ to the dose rate $D_0$ in the comparative case, in which the operating method of this embodiment is not applied, is expressed by the following formula (6):

$$\frac{D_2}{D_0} = \frac{Q}{T+T_{ex}} \frac{T+T_{ex}}{aQ} = \frac{1}{a} \quad (6)$$

As seen from the above formula, an increase of the dose rate is inversely proportional to the duty a without depending on both the extraction enable time and the other time than the extraction enable time, and the dose rate is increased as the duty a increases.

In order to hold constant the amount of the ion beam extracted per cycle, the above-described second embodiment employs means for increasing the RF output applied to the RF knockout electrode 7 for the extraction of the ion beam. However, there is a possibility that, for example, when the state of the synchrotron 4 per cycle is unstable, the ion beam may be extracted in a shorter time, or one cycle may be terminated before the ion beam is extracted in predetermined amount. In consideration of such a possibility, the second embodiment may be modified to include means for previously setting, in the irradiation control section 71, a dose output value corresponding to the amount of the ion beam to be extracted per cycle, which is obtained, for example, from the dose monitor 31 shown in FIG. 1, and continuing the irradiation when the integrated value of the dose detected per cycle is within the set dose value, or stopping the irradiation when the integrated dose value exceeds the set dose value, followed by a shift to the deceleration step.

In the case of the synchrotron 4 having a large setting value of the beam energy, the output of the RF power supply may become insufficient because a large RF output is required to realize the above-described irradiation in this embodiment. To avoid such a trouble, it is also possible to perform both the operations of the first embodiment and the second embodiment in a combined manner, i.e., to execute not only the control for prolonging the extraction time depending on an increase of the RF output, but also the control for holding the amount of the ion beam extracted per cycle substantially at the setting value, i.e., substantially constant.

Third Embodiment

Figure 12:
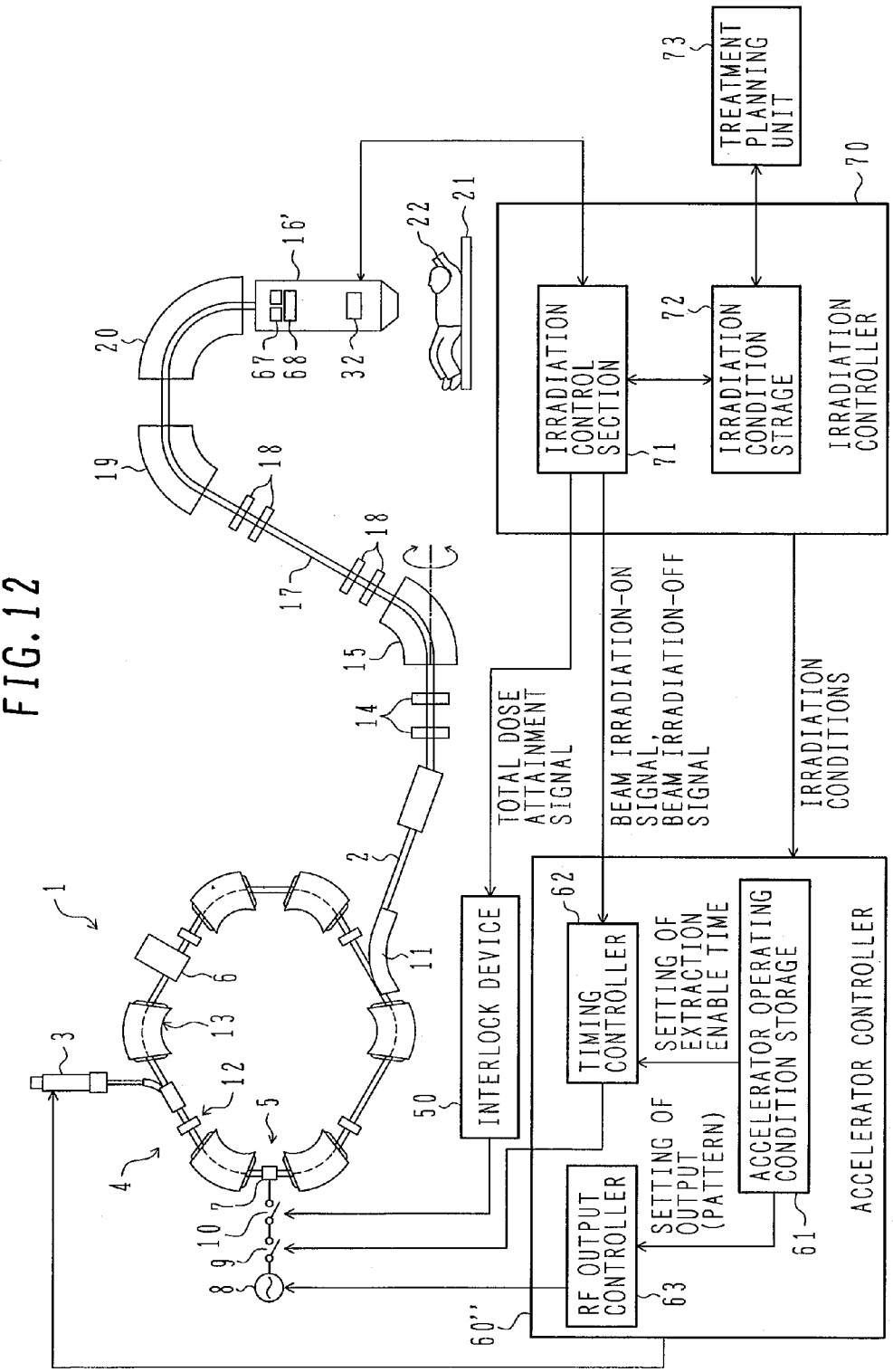
FIG. 12 is a block diagram showing a schematic overall construction of a charged particle beam extraction system according to a third embodiment of the present invention.

A charged particle beam extraction system according to still another preferred embodiment of the present invention will be described below as a third embodiment with reference to FIG. 12. In this embodiment, the present invention is applied to a charged particle beam extraction system of scanning irradiation type.

The charged particle beam extraction system of this embodiment includes an irradiation device 16' for performing pencil-beam scanning irradiation such that a pencil-shaped small-diameter beam is scanned in match with the shape of the diseased part. The irradiation device 16' scans an ion beam in a planar direction perpendicular to the direction of travel of the beam by using beam scanning magnets 67, 68. According to this irradiation technique, an irradiation area is divided into small targets (hereinafter referred to as "spots"), and the irradiation is performed by repeating the operations of stopping the beam when the beam has been irradiated in preset dose to one spot, starting a next cycle of irradiation as soon as after preparations for the irradiation to the next spot have been finished, stopping the beam when the beam has been irradiated in preset dose to the next spot, and making preparations for the irradiation to the subsequent spot again. The movement of the ion beam in the direction of depth into the body, i.e., in the direction of travel of the beam, is made by changing the energy of the ion beam extracted from the synchrotron 4. When changing the energy of the ion beam, the operation of the synchrotron 4 is started from the introduction step, and the ion beam is extracted after accelerating the beam to a desired level of energy. The dose per spot is measured by the dose monitor 32, and the irradiation is stopped when the dose limit value is detected per spot. The irradiation is then restarted in a state where preparations of the beam scanning magnets 67, 68 are completed.

Range control in the direction of depth into the body is executed by changing the setting of the RF power applied to the accelerator 6 so that the setting of the target energy of the synchrotron 4 is successively changed. More specifically, the diseased part is divided into a plurality of layers in the direction of depth into the body, and after the irradiation to all the spots in each layer is completed, the setting of the target energy of the synchrotron 4 is changed, followed by a shift to a next layer. In the same layer, the individual spots are successively irradiated by repeating the operations of irradiating and stopping the beam at the same energy. Regarding the spots irradiated at the same energy, the irradiation is performed in each cycle of the synchrotron 4. Accordingly, when the scanning irradiation is performed as in this embodiment, the beam-on/off control is executed during the extraction step in each cycle.

In this embodiment, the irradiation control section 71 produces the beam irradiation-off signal upon detection of the dose limit per spot and the beam irradiation-on signal for starting the irradiation to the next spot, these signals being both outputted to the timing controller 62 in an accelerator controller 60". The timing controller 62 includes a timer (not shown) for integrating the beam irradiation-off/on signals, to thereby integrate the time during which the beam irradiation-on signal has been inputted. On the other hand, the timing controller 62 sets the extraction enable time as a part of the accelerator operating conditions. While the extraction enable time is set based on the duty a computed from the cyclic rotational angle information of the RMW 40 in the first and second embodiments described above, it is set in this embodiment based on the irradiation conditions (treatment plan information) decided in the treatment planning unit 73 because the setting dose per spot, changes of the beam intensity in a short period, and the setting time between the spots are not always constant in this embodiment.

Then, the integrated beam signal-on time is compared with the set extraction enable time, and if the integrated time is within the extraction enable time, the beam is irradiated in response to the beam irradiation-on signal. More specifically, the beam irradiation-on signal is outputted to the on/off switch 9, thereby closing the on/off switch 9. Responsively, the RF wave supplied from the RF power supply 8 for extracting the ion beam is applied to the RF knockout electrode 7 through the closed on/off switches 9, 10 (the on/off switch 10 being assumed to be now closed), and is then applied to the ion beam from the RF knockout electrode 7. With the application of the RF wave, the ion beam circulating within the separatrix is forced to transit out of the separatrix and to exit from the synchrotron 4 through the extraction deflector 11. The ion beam extracted from the synchrotron 4 is transported through the beam line 2 to the irradiation device 16' and is then irradiated to the spot in a predetermined position while being scanned by the scanning magnets 67, 68.

When a limit of the spot dose is detected, the timing controller 62 outputs the beam irradiation-off signal to the on/off switch 9 in response to the beam irradiation-off signal from the irradiation control section 71. The on/off switch 9 is thereby opened. Responsively, the application of the RF power to the RF knockout electrode 7 is stopped and the extraction of the ion beam from the synchrotron 4 is stopped. Then, the irradiation control section 71 changes the setting of the scanning magnets 67, 68 to that adapted for irradiation to the next spot, and the beam irradiation-on signal is outputted again to the timing controller 62.

If the total time of the beam irradiation-on signal integrated by the timing controller 62 reaches the extraction enable time, the on/off switch 9 is opened to stop the beam extraction from the synchrotron 4, and the operation is immediately shifted to the deceleration step.

Also, the operation is immediately shifted to the deceleration step upon the completion of the irradiation to all the spots to which the ion beam is to be irradiated at the same energy (i.e., all the spots in the same layer) with respect to the direction of depth into the body. Further, because the total dose necessary for one plan of treatment irradiation to the patient 22 is decided before the start of the treatment, attainment of the dose is determined from the viewpoint of safety when the integrated value of the dose measured by, e.g., the dose monitor 32 reaches the decided dose. Responsively, the on/off switch 10 is opened through the interlock device 50 to stop the application of the RF output to the RF knockout electrode 7, whereby the beam extraction is stopped.

With this embodiment described above, the control is also executed so as to prolong the time of the extraction time in each cycle. Therefore, even when the operations of extracting the beam and stopping the extraction are repeatedly performed during the extraction step according to the pencil beam scanning method, the amount of the beam extracted from the synchrotron 4 in each cycle can be held substantially at a setting value without causing a reduction of the beam amount. Accordingly, the irradiation time can be cut and the number of patients treatable per unit time can be increased as in the first and second embodiments.

Fourth Embodiment

Figure 13:
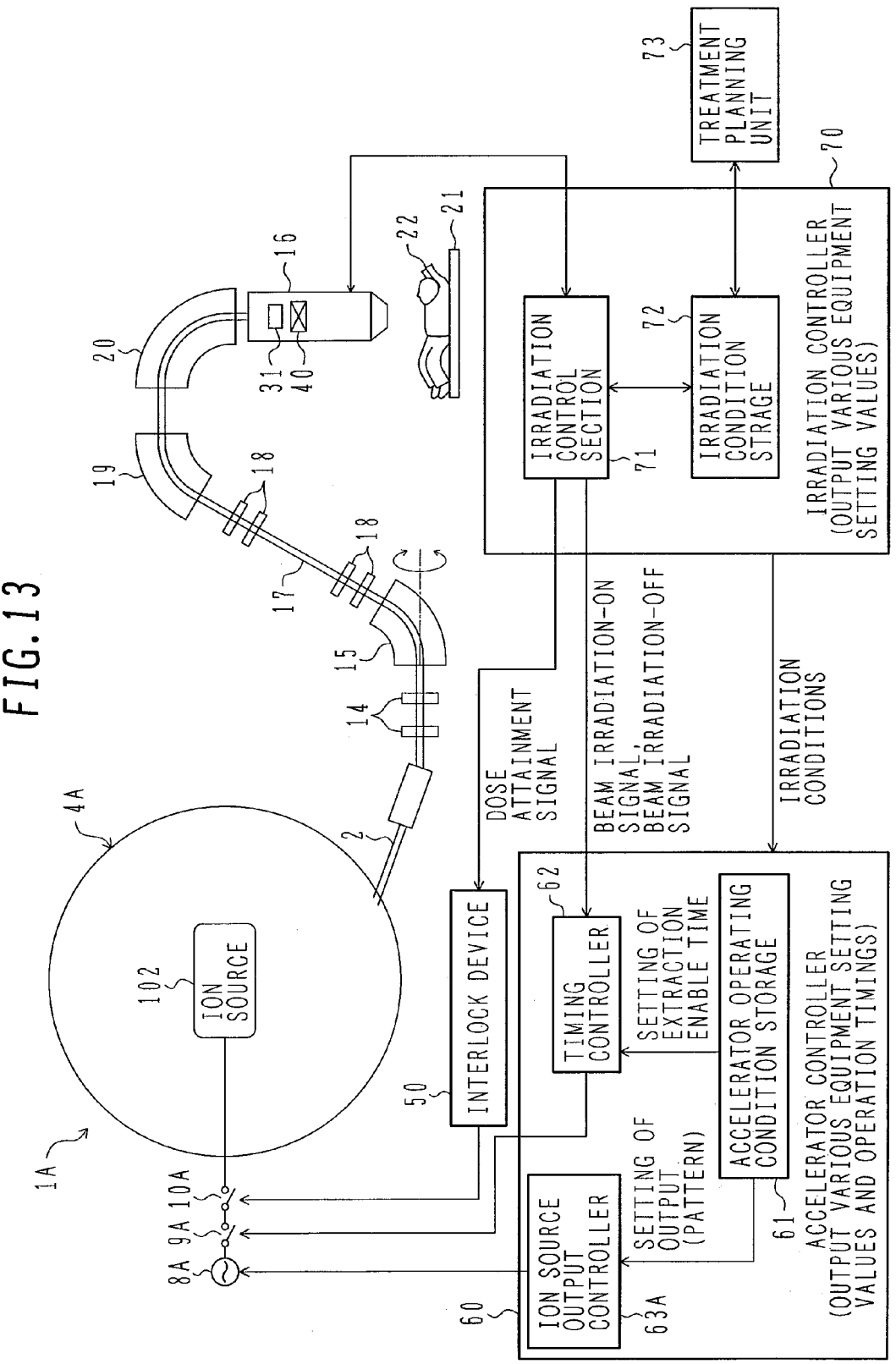
FIG. 13 is a block diagram showing a schematic overall construction of a charged particle beam extraction system according to a fourth embodiment of the present invention.

While the above-described third and fourth embodiments use a synchrotron as the accelerator, the present invention is also applicable to a charged particle beam extraction system using a cyclotron as the accelerator. The charged particle beam extraction system using a cyclotron as the accelerator will be described below with reference to FIG. 13.

The charged particle beam extraction system of this fourth embodiment is constituted by modifying the charged particle beam extraction system of the second embodiment such that the ion beam generator 1 is replaced with an ion beam generator 1A, an RF output controller 63 is replaced with an ion source output controller 63A, and an energy changing device 101 is newly provided. The other configuration of the charged particle beam extraction system of the fourth embodiment is the same as that of the second embodiment. Also, this fourth embodiment uses an irradiation device 16 that forms an irradiation field using an RMW and performs irradiation.

The ion beam generator 1A comprises a cyclotron (accelerator) 4A, an ion source 102, an ion-source output adjusting unit 8A, a switch 9A, and a switch 10A. The cyclotron 4A includes an accelerating apparatus (not shown). The energy changing device 101 is disposed in a beam line 2 at a position near the cyclotron 4A. The energy changing device 101 comprises a plurality of plate-like degraders (not shown) through which an ion beam passes with loss of energy, a bending magnet (not shown) for bending the ion beam having reduced energy, an aperture (not shown) for cutting out a part of the ion beam having passed the bending magnet, etc. The plurality of degraders disposed in the energy changing device 101 have different values of thickness to provide plural levels of energy. The energy of the ion beam is changed with the passage of the ion beam through the degraders. Because the cyclotron 4A continues to accelerate and extract the ion beam generated from the ion source 102, it has not the introduction, acceleration and extraction steps which are performed in the synchrotron 4. An adjustment of the intensity of the ion beam extracted from the cyclotron 4A and turning-on/off of the extraction of the ion beam are performed by adjusting and turning on/off an output of the ion source 102.

The accelerator controller 60 includes an ion source output controller 63A for controlling an output of the ion-source output adjusting unit 8A. The switch 9A is turned on/off by a timing controller 62 for controlling the timing at which the beam irradiation-on/off signal is to be received with the rotation of the RMW 40. The switch 10A is turned on/off by an interlock device 50 for stopping the beam extraction in accordance with the detection of limit dose or other various interlock conditions. The switch 9A and the switch 10A have the function of turning on/off the output applied from the ion-source output adjusting unit 8A to the ion source 102, to thereby turn on/off the ion source output.

As described above, the SOBP data stored as the irradiation conditions in the irradiation condition storage 72 of the irradiation controller 70 contains the type of the RMW 40 and the beam irradiation area information (namely, information representing in which area (rotational angle range) of the RMW 40 the beam is to be turned on/off)). The relations of the SOBP with respect to the type of the RMW 40 and the beam irradiation area information are determined in advance through calculations, experiments, etc. In this fourth embodiment, as in the second embodiment, the ion source output controller 63A computes the duty a, i.e., the turned-on time of the beam irradiation signal, based on irradiation start angle information and irradiation stop angle information for the RMW 40, which are contained in the irradiation conditions. Alternatively, as in the first embodiment, the duty a may be computed by the timing controller 62 and inputted to the ion source output controller 63A. In accordance with the computed duty a, the ion source output controller 63A executes control to increase the output of the ion-source output adjusting unit 8A so that the amount of the ion beam extracted in a certain period, e.g., one cycle one cycle of the RMW rotation, is held substantially at a setting value.

With the above-described charged particle beam extraction system of this embodiment, the output from the ion source 102 is controlled to increase depending on the duty a. Therefore, even when the operations of extracting the beam and stopping the extraction are repeatedly performed during one rotation cycle of the RMW 40, the amount of the beam extracted from the synchrotron 4 in each cycle can be held substantially at the setting value without causing a reduction of the beam amount. Accordingly, this fourth embodiment enables the irradiation time to be cut as in the first and second embodiments. As a result, the number of patients treatable per unit time can be increased.

Further, this fourth embodiment can also increase the dose rate of the charged particle beam extraction system. This point will be described below with reference to FIG. 14. In the irradiation executed in this fourth embodiment, the beam is extracted from the cyclotron 4A in a way not being cyclic, but substantially constant. Assuming an extracted current value to be $I_0$, when the beam irradiation is not turned on/off with the RMW rotation, a dose rate $D_0$ is in proportion to the current value and can be expressed as given below (see (a) in FIG. 14):

$$D_0 = K'I_0 \tag{7}$$

When the beam irradiation is turned on/off with the RMW rotation at the duty of a, a dose rate $D_3$ is reduced in proportion to the duty a and is expressed as given below (see (b) in FIG. 14) if this fourth embodiment is not applied and the beam is irradiated without changing the ion source output:

$$D_3 = K' \times aI_0$$

In this fourth embodiment, the ion source output is increased depending on the duty a to increase the current value of the extracted beam. Stated another way, because the current value is increased to $I_0/a$, a dose rate $D_3'$ is expressed as given below and remains the same as that resulting from when the beam irradiation is turned on/off with the RMW rotation:

$$D_3' = K' \times a \times \frac{I_0}{a} = K'I_0$$

Determining a ratio between the dose rate $D_3$ resulting when the operating method of this fourth embodiment is not applied and the dose rate $D_3'$ resulting when it is not applied, the ratio is expressed by:

$$\frac{D_3'}{D_3} = \frac{K'I_0}{K' \times aI_0} = \frac{1}{a}$$

As seen from the above formula, an increase of the dose rate is in inverse proportion to the duty a. Namely, the smaller the duty, the larger is the dose rate.

While, this fourth embodiment has been described as increasing the ion source output, i.e., the current value, at a ratio of 1/a, there is a possibility that the increased current value $I_0/a$ may reach an upper limit value of the ion source output, i.e., an upper limit value of the current value of the extracted beam. In such a case, the beam is irradiated with the current value set to the upper limit value.

What is claimed is:

1. A charged particle beam extraction system for extracting a charged particle beam through an irradiation device, said charged particle beam extraction system comprising:
    an accelerator for cyclically performing patterned operation including steps of introducing, accelerating and extracting the charged particle beam;
    an amount-of-extracted beam adjusting unit for changing an amount of the charged particle beam extracted from said accelerator; and
    a control unit for controlling said amount-of-extracted beam adjusting unit such that when extraction of the charged particle beam is stopped at least once during the extraction step of said accelerator, the amount of the charged particle beam extracted from said accelerator in one cycle is held substantially at a setting value of the amount of extracted beam.

2. The charged particle beam extraction system according to claim 1, wherein said control unit controls said amount-of-extracted beam adjusting unit, said extraction time adjusting unit, or said beam intensity adjusting unit based on treatment plan information.

3. The charged particle beam extraction system according to claim 1, wherein said control unit controls said amount-of-extracted beam adjusting unit, said extraction time adjusting unit, or said beam intensity adjusting unit in accordance with a ratio of a beam extraction time to an extraction stopped time during the extraction step of said accelerator.

4. A charged particle beam extraction system for extracting a charged particle beam through an irradiation device, said charged particle beam extraction system comprising:
    an accelerator for cyclically performing patterned operation including steps of introducing, accelerating and extracting the charged particle beam;
    an extraction time adjusting unit for changing a time of the extraction step of said accelerator; and
    a control unit for controlling said extraction time adjusting unit such that when extraction of the charged particle beam is stopped at least once during the extraction step of said accelerator, an amount of the charged particle beam extracted from said accelerator in one cycle is held substantially at a setting value of the amount of extracted beam.

5. The charged particle beam extraction system according to claim 4, wherein said control unit includes an extraction enable time setting unit for setting an extraction enable time of the charged particle beam from said accelerator in accordance with a ratio of a beam extraction time to an extraction stopped time during the extraction step of said accelerator, an integrating unit for integrating a time during which the charged particle beam has been extracted from said accelerator, and a determining unit for determining whether the integrated beam extraction time has reached the set extraction enable time.

6. The charged particle beam extraction system according to claim 5, further comprising an extraction stopping device for stopping the extraction of the charged particle beam from said accelerator when said determining unit determines whether the integrated beam extraction time has reached the set extraction enable time.

7. A charged particle beam extraction system for extracting a charged particle beam through an irradiation device, said charged particle beam extraction system comprising:
    an accelerator for cyclically performing patterned operation including steps of introducing, accelerating and extracting the charged particle beam;
    a beam intensity adjusting unit for changing the intensity of the charged particle beam extracted from said accelerator; and
    a control unit for controlling said beam intensity adjusting unit such that when extraction of the charged particle beam is stopped at least once during the extraction step of said accelerator, an amount of the charged particle beam extracted from said accelerator in one cycle is held substantially at a setting value of the amount of extracted beam.

8. The charged particle beam extraction system according to claim 7, wherein said control unit includes a beam intensity setting unit for setting the intensity of the charged particle beam extracted from said accelerator in accordance with a ratio of a beam extraction time to an extraction stopped time during the extraction step of said accelerator, and an RF output control unit for controlling an RF output applied to the charged particle beam circulating inside said accelerator such that the set beam intensity is obtained.

9. A charged particle beam extraction method for extracting, through an irradiation device, a charged particle beam extracted from an accelerator for cyclically performing patterned operation including steps of introducing, accelerating and extracting the charged particle beam, the method including a step of making control such that when extraction of the charged particle beam is stopped at least once during the extraction step of said accelerator, an amount of the charged particle beam extracted from said accelerator in one cycle is held substantially at a setting value of the amount of extracted beam.

10. A charged particle beam extraction method for extracting, through an irradiation device, a charged particle beam extracted from an accelerator for cyclically performing patterned operation including steps of introducing, accelerating and extracting the charged particle beam, the method including a step of changing a time of the extraction step of said accelerator such that when extraction of the charged particle beam is stopped at least once during the extraction step of said accelerator, an amount of the charged particle beam extracted from said accelerator in one cycle is held substantially at a setting value of the amount of extracted beam.

11. A charged particle beam extraction method for extracting, through an irradiation device, a charged particle beam extracted from an accelerator for cyclically performing patterned operation including steps of introducing, accelerating and extracting the charged particle beam, the method including a step of changing the intensity of the charged particle beam extracted from said accelerator such that when extraction of the charged particle beam is stopped at least once during the extraction step of said accelerator, an amount of the charged particle beam extracted from said accelerator in one cycle is held substantially at a setting value of the amount of extracted beam.

12. A charged particle beam extraction system for extracting a charged particle beam through an irradiation device, said charged particle beam extraction system comprising:

an accelerator for cyclically extracting and stopping the charged particle beam;

a beam intensity adjusting unit for changing the intensity of the charged particle beam extracted from said accelerator; and a control unit for controlling said beam intensity adjusting unit such that when extraction of the charged particle beam extracted from said accelerator is stopped in a certain cycle, an amount of the charged particle beam extracted from said accelerator in that cycle is held substantially at a setting value of the amount of extracted beam.

* * * * *